(12) United States Patent
DeCarlo et al.

(10) Patent No.: US 7,141,551 B1
(45) Date of Patent: Nov. 28, 2006

(54) WOUND AND CUTANEOUS INJURY HEALING WITH A NUCLEIC ACID ENCODING PERLECAN

(76) Inventors: Arthur A. DeCarlo, 783 Lavender Cir., Weston, FL (US) 33326; John Whitelock, 16 Smallwood Ave., Homebush 2140, Sydney (AU)

( * ) Notice: Subject to any disclaimer, the term of this patent is extended or adjusted under 35 U.S.C. 154(b) by 0 days.

(21) Appl. No.: 10/420,270

(22) Filed: Apr. 22, 2003

(51) Int. Cl.
*A61K 31/70* (2006.01)
*A01N 63/00* (2006.01)
(52) U.S. Cl. .................. 514/44; 424/93.2; 424/450
(58) Field of Classification Search .................. 514/44; 424/93.1, 93.2, 450; 435/320.1
See application file for complete search history.

(56) References Cited

OTHER PUBLICATIONS

Groffen et al. Expression and Characterization of Human Perlecan Domains I and II Synthesized by Baculovirus-Infected Insect Cells. Eur. J. Biochem. 241, pp. 827-834.*
Nugent et al. Fibroblast Growth Factor-2. International J. Biochem. Cell Biol. 2000, vol. 32, pp. 115-120.*
Zhao et al. Adenovirus-Mediated Decorin Gene Transfer Prevents TGF-Beta Induced Inhibition of Lung Morphogenesis. American. J. Physiol., vol. 277 (Lung Cell. Mol. Phys. 21), pp. L412-L422.*

* cited by examiner

*Primary Examiner*—Deborah Crouch
(74) *Attorney, Agent, or Firm*—Bradley, Arant, Rose & White, LLP

(57) ABSTRACT

A description of a biomolecule named Perlecan which is added internally or topically, or is expressed from exogenously added nucleic acids, as a whole or in part, to a healing wound to improve the success of wound healing is disclosed. Relevant embodiments for this patent technology are described.

3 Claims, No Drawings

SEQUENCE LISTING

<160> NUMBER OF SEQ ID NOS: 5

<210> SEQ ID NO 1
<211> LENGTH: 13
<212> TYPE: PRT
<213> ORGANISM: Homo sapiens

<400> SEQUENCE: 1

Leu Pro Ala Ser Phe Arg Gly Asp Lys Val Thr Ser Tyr

-continued

```
1               5               10
```

<210> SEQ ID NO 2
<211> LENGTH: 6
<212> TYPE: PRT
<213> ORGANISM: Homo sapiens

<400> SEQUENCE: 2

```
Gly Arg Gly Asp Ser Pro
1               5
```

<210> SEQ ID NO 3
<211> LENGTH: 6
<212> TYPE: PRT
<213> ORGANISM: Homo sapiens

<400> SEQUENCE: 3

```
Gly Arg Gly Glu Ser Pro
1               5
```

<210> SEQ ID NO 4
<211> LENGTH: 4391
<212> TYPE: PRT
<213> ORGANISM: Homo sapiens

<400> SEQUENCE: 4

```
Met Gly Trp Arg Ala Pro Gly Ala Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
            35                  40                  45

Thr His Ser Tyr Leu Ser Asp Asp Glu Tyr Met Leu Ala Asp Ser Ile
            50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
            115                 120                 125

Asp Gln Val Val Ser Val Val Phe Ile Lys Glu Leu Asp Gly Trp Val
            130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Glu Phe Ala Cys His Ser
            195                 200                 205

Tyr Asn Glu Cys Val Ala Leu Glu Tyr Arg Cys Asp Arg Arg Pro Asp
            210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
                245                 250                 255
```

-continued

```
Arg Pro Glu Thr Thr Ile Met Arg Gln Pro Val Thr His Ala Pro
            260                 265                 270
Gln Pro Leu Leu Pro Gly Ser Val Arg Pro Leu Pro Cys Gly Pro Gln
        275                 280                 285
Glu Ala Ala Cys Arg Asn Gly His Cys Ile Pro Arg Asp Tyr Leu Cys
    290                 295                 300
Asp Gly Gln Glu Asp Cys Glu Asp Gly Ser Asp Glu Leu Asp Cys Gly
305                 310                 315                 320
Pro Pro Pro Pro Cys Glu Pro Asn Glu Phe Pro Cys Gly Asn Gly His
                325                 330                 335
Cys Ala Leu Lys Leu Trp Arg Cys Asp Gly Asp Phe Asp Cys Glu Asp
            340                 345                 350
Arg Thr Asp Glu Ala Asn Cys Pro Thr Lys Arg Pro Glu Glu Val Cys
        355                 360                 365
Gly Pro Thr Gln Phe Arg Cys Val Ser Thr Asn Met Cys Ile Pro Ala
    370                 375                 380
Ser Phe His Cys Asp Glu Glu Ser Asp Cys Pro Asp Arg Ser Asp Glu
385                 390                 395                 400
Phe Gly Cys Met Pro Pro Gln Val Val Thr Pro Pro Arg Glu Ser Ile
                405                 410                 415
Gln Ala Ser Arg Gly Gln Thr Val Thr Phe Thr Cys Val Ala Ile Gly
            420                 425                 430
Val Pro Thr Pro Ile Ile Asn Trp Arg Leu Asn Trp Gly His Ile Pro
        435                 440                 445
Ser His Pro Arg Val Thr Val Thr Ser Glu Gly Gly Arg Gly Thr Leu
    450                 455                 460
Ile Ile Arg Asp Val Lys Glu Ser Asp Gln Gly Ala Tyr Thr Cys Glu
465                 470                 475                 480
Ala Met Asn Ala Arg Gly Met Val Phe Gly Ile Pro Asp Gly Val Leu
                485                 490                 495
Glu Leu Val Pro Gln Arg Gly Pro Cys Pro Asp Gly His Phe Tyr Leu
            500                 505                 510
Glu His Ser Ala Ala Cys Leu Pro Cys Phe Cys Phe Gly Ile Thr Ser
        515                 520                 525
Val Cys Gln Ser Thr Arg Arg Phe Arg Asp Gln Ile Arg Leu Arg Phe
    530                 535                 540
Asp Gln Pro Asp Asp Phe Lys Gly Val Asn Val Thr Met Pro Ala Gln
545                 550                 555                 560
Pro Gly Thr Pro Pro Leu Ser Ser Thr Gln Leu Gln Ile Asp Pro Ser
                565                 570                 575
Leu His Glu Phe Gln Leu Val Asp Leu Ser Arg Arg Phe Leu Val His
            580                 585                 590
Asp Ser Phe Trp Ala Leu Pro Glu Gln Phe Leu Gly Asn Lys Val Asp
        595                 600                 605
Ser Tyr Gly Gly Ser Leu Arg Tyr Asn Val Arg Tyr Glu Leu Ala Arg
    610                 615                 620
Gly Met Leu Glu Pro Val Gln Arg Pro Asp Val Val Leu Val Gly Ala
625                 630                 635                 640
Gly Tyr Arg Leu Leu Ser Arg Gly His Thr Pro Thr Gln Pro Gly Ala
                645                 650                 655
Leu Asn Gln Arg Gln Val Gln Phe Ser Glu Glu His Trp Val His Glu
            660                 665                 670
```

```
Ser Gly Arg Pro Val Gln Arg Ala Glu Leu Leu Gln Val Leu Gln Ser
        675                 680                 685

Leu Glu Ala Val Leu Ile Gln Thr Val Tyr Asn Thr Lys Met Ala Ser
    690                 695                 700

Val Gly Leu Ser Asp Ile Ala Met Asp Thr Thr Val Thr His Ala Thr
705                 710                 715                 720

Ser His Gly Arg Ala His Ser Val Glu Glu Cys Arg Cys Pro Ile Gly
                725                 730                 735

Tyr Ser Gly Leu Ser Cys Glu Ser Cys Asp Ala His Phe Thr Arg Val
            740                 745                 750

Pro Gly Gly Pro Tyr Leu Gly Thr Cys Ser Gly Cys Ser Cys Asn Gly
        755                 760                 765

His Ala Ser Ser Cys Asp Pro Val Tyr Gly His Cys Leu Asn Cys Gln
770                 775                 780

His Asn Thr Glu Gly Pro Gln Cys Asn Lys Cys Lys Ala Gly Phe Phe
785                 790                 795                 800

Gly Asp Ala Met Lys Ala Thr Ala Thr Ser Cys Arg Pro Cys Pro Cys
                805                 810                 815

Pro Tyr Ile Asp Ala Ser Arg Arg Phe Ser Asp Thr Cys Phe Leu Asp
            820                 825                 830

Thr Asp Gly Gln Ala Thr Cys Asp Ala Cys Ala Pro Gly Tyr Thr Gly
        835                 840                 845

Arg Arg Cys Glu Ser Cys Ala Pro Gly Tyr Glu Gly Asn Pro Ile Gln
850                 855                 860

Pro Gly Gly Lys Cys Arg Pro Val Asn Gln Glu Ile Val Arg Cys Asp
865                 870                 875                 880

Glu Arg Gly Ser Met Gly Thr Ser Gly Glu Ala Cys Arg Cys Lys Asn
                885                 890                 895

Asn Val Val Gly Arg Leu Cys Asn Glu Cys Ala Asp Gly Ser Phe His
            900                 905                 910

Leu Ser Thr Arg Asn Pro Asp Gly Cys Leu Lys Cys Phe Cys Met Gly
        915                 920                 925

Val Ser Arg His Cys Thr Ser Ser Ser Trp Ser Arg Ala Gln Leu His
930                 935                 940

Gly Ala Ser Glu Glu Pro Gly His Phe Ser Leu Thr Asn Ala Ala Ser
945                 950                 955                 960

Thr His Thr Thr Asn Glu Gly Ile Phe Ser Pro Thr Pro Gly Glu Leu
                965                 970                 975

Gly Phe Ser Ser Phe His Arg Leu Leu Ser Gly Pro Tyr Phe Trp Ser
            980                 985                 990

Leu Pro Ser Arg Phe Leu Gly Asp Lys Val Thr Ser Tyr Gly Gly Glu
        995                 1000                1005

Leu Arg Phe Thr Val Thr Gln Arg Ser Gln Pro Gly Ser Thr Pro
    1010                1015                1020

Leu His Gly Gln Pro Leu Val Val Leu Gln Gly Asn Asn Ile Ile
    1025                1030                1035

Leu Glu His His Val Ala Gln Glu Pro Ser Pro Gly Gln Pro Ser
    1040                1045                1050

Thr Phe Ile Val Pro Phe Arg Glu Gln Ala Trp Gln Arg Pro Asp
    1055                1060                1065

Gly Gln Pro Ala Thr Arg Glu His Leu Leu Met Ala Leu Ala Gly
    1070                1075                1080

Ile Asp Thr Leu Leu Ile Arg Ala Ser Tyr Ala Gln Gln Pro Ala
```

-continued

|  | 1085 |  |  |  | 1090 |  |  |  |  | 1095 |  |
| --- | --- | --- | --- | --- | --- | --- | --- | --- | --- | --- | --- |
| Glu | Ser | Arg | Val | Ser | Gly | Ile | Ser | Met | Asp | Val | Ala | Val | Pro | Glu |
| | 1100 | | | | | 1105 | | | | | 1110 | | | |
| Glu | Thr | Gly | Gln | Asp | Pro | Ala | Leu | Glu | Val | Glu | Gln | Cys | Ser | Cys |
| | 1115 | | | | | 1120 | | | | | 1125 | | | |
| Pro | Pro | Gly | Tyr | Arg | Gly | Pro | Ser | Cys | Gln | Asp | Cys | Asp | Thr | Gly |
| | 1130 | | | | | 1135 | | | | | 1140 | | | |
| Tyr | Thr | Arg | Thr | Pro | Ser | Gly | Leu | Tyr | Leu | Gly | Thr | Cys | Glu | Arg |
| | 1145 | | | | | 1150 | | | | | 1155 | | | |
| Cys | Ser | Cys | His | Gly | His | Ser | Glu | Ala | Cys | Glu | Pro | Glu | Thr | Gly |
| | 1160 | | | | | 1165 | | | | | 1170 | | | |
| Ala | Cys | Gln | Gly | Cys | Gln | His | His | Thr | Glu | Gly | Pro | Arg | Cys | Glu |
| | 1175 | | | | | 1180 | | | | | 1185 | | | |
| Gln | Cys | Gln | Pro | Gly | Tyr | Tyr | Gly | Asp | Ala | Gln | Arg | Gly | Thr | Pro |
| | 1190 | | | | | 1195 | | | | | 1200 | | | |
| Gln | Asp | Cys | Gln | Leu | Cys | Pro | Cys | Tyr | Gly | Asp | Pro | Ala | Ala | Gly |
| | 1205 | | | | | 1210 | | | | | 1215 | | | |
| Gln | Ala | Ala | His | Thr | Cys | Phe | Leu | Asp | Thr | Asp | Gly | His | Pro | Thr |
| | 1220 | | | | | 1225 | | | | | 1230 | | | |
| Cys | Asp | Ala | Cys | Ser | Pro | Gly | His | Ser | Gly | Arg | His | Cys | Glu | Arg |
| | 1235 | | | | | 1240 | | | | | 1245 | | | |
| Cys | Ala | Pro | Gly | Tyr | Tyr | Gly | Asn | Pro | Ser | Gln | Gly | Gln | Pro | Cys |
| | 1250 | | | | | 1255 | | | | | 1260 | | | |
| Gln | Arg | Asp | Ser | Gln | Val | Pro | Gly | Pro | Ile | Gly | Cys | Asn | Cys | Asp |
| | 1265 | | | | | 1270 | | | | | 1275 | | | |
| Pro | Gln | Gly | Ser | Val | Ser | Ser | Gln | Cys | Asp | Ala | Ala | Gly | Gln | Cys |
| | 1280 | | | | | 1285 | | | | | 1290 | | | |
| Gln | Cys | Lys | Ala | Gln | Val | Glu | Gly | Leu | Thr | Cys | Ser | His | Cys | Arg |
| | 1295 | | | | | 1300 | | | | | 1305 | | | |
| Pro | His | His | Phe | His | Leu | Ser | Ala | Ser | Asn | Pro | Asp | Gly | Cys | Leu |
| | 1310 | | | | | 1315 | | | | | 1320 | | | |
| Pro | Cys | Phe | Cys | Met | Gly | Ile | Thr | Gln | Gln | Cys | Ala | Ser | Ser | Ala |
| | 1325 | | | | | 1330 | | | | | 1335 | | | |
| Tyr | Thr | Arg | His | Leu | Ile | Ser | Thr | His | Phe | Ala | Pro | Gly | Asp | Phe |
| | 1340 | | | | | 1345 | | | | | 1350 | | | |
| Gln | Gly | Phe | Ala | Leu | Val | Asn | Pro | Gln | Arg | Asn | Ser | Arg | Leu | Thr |
| | 1355 | | | | | 1360 | | | | | 1365 | | | |
| Gly | Glu | Phe | Thr | Val | Glu | Pro | Val | Pro | Glu | Gly | Ala | Gln | Leu | Ser |
| | 1370 | | | | | 1375 | | | | | 1380 | | | |
| Phe | Gly | Asn | Phe | Ala | Gln | Leu | Gly | His | Glu | Ser | Phe | Tyr | Trp | Gln |
| | 1385 | | | | | 1390 | | | | | 1395 | | | |
| Leu | Pro | Glu | Thr | Tyr | Gln | Gly | Asp | Lys | Val | Ala | Ala | Tyr | Gly | Gly |
| | 1400 | | | | | 1405 | | | | | 1410 | | | |
| Lys | Leu | Arg | Tyr | Thr | Leu | Ser | Tyr | Thr | Ala | Gly | Pro | Gln | Gly | Ser |
| | 1415 | | | | | 1420 | | | | | 1425 | | | |
| Pro | Leu | Ser | Asp | Pro | Asp | Val | Gln | Ile | Thr | Gly | Asn | Asn | Ile | Met |
| | 1430 | | | | | 1435 | | | | | 1440 | | | |
| Leu | Val | Ala | Ser | Gln | Pro | Ala | Leu | Gln | Gly | Pro | Glu | Arg | Arg | Ser |
| | 1445 | | | | | 1450 | | | | | 1455 | | | |
| Tyr | Glu | Ile | Met | Phe | Arg | Glu | Glu | Phe | Trp | Arg | Arg | Pro | Asp | Gly |
| | 1460 | | | | | 1465 | | | | | 1470 | | | |
| Gln | Pro | Ala | Thr | Arg | Glu | His | Leu | Leu | Met | Ala | Leu | Ala | Asp | Leu |
| | 1475 | | | | | 1480 | | | | | 1485 | | | |

-continued

```
Asp Glu Leu Leu Ile Arg Ala Thr Phe Ser Ser Val Pro Leu Val
    1490            1495                1500

Ala Ser Ile Ser Ala Val Ser Leu Glu Val Ala Gln Pro Gly Pro
    1505            1510                1515

Ser Asn Arg Pro Arg Ala Leu Glu Val Glu Glu Cys Arg Cys Pro
    1520            1525                1530

Pro Gly Tyr Ile Gly Leu Ser Cys Gln Asp Cys Ala Pro Gly Tyr
    1535            1540                1545

Thr Arg Thr Gly Ser Gly Leu Tyr Leu Gly His Cys Glu Leu Cys
    1550            1555                1560

Glu Cys Asn Gly His Ser Asp Leu Cys His Pro Glu Thr Gly Ala
    1565            1570                1575

Cys Ser Gln Cys Gln His Asn Ala Ala Gly Glu Phe Cys Glu Leu
    1580            1585                1590

Cys Ala Pro Gly Tyr Tyr Gly Asp Ala Thr Ala Gly Thr Pro Glu
    1595            1600                1605

Asp Cys Gln Pro Cys Ala Cys Pro Leu Thr Asn Pro Glu Asn Met
    1610            1615                1620

Phe Ser Arg Thr Cys Glu Ser Leu Gly Ala Gly Gly Tyr Arg Cys
    1625            1630                1635

Thr Ala Cys Glu Pro Gly Tyr Thr Gly Gln Tyr Cys Glu Gln Cys
    1640            1645                1650

Gly Pro Gly Tyr Val Gly Asn Pro Ser Val Gln Gly Gly Gln Cys
    1655            1660                1665

Leu Pro Glu Thr Asn Gln Ala Pro Leu Val Val Glu Val His Pro
    1670            1675                1680

Ala Arg Ser Ile Val Pro Gln Gly Gly Ser His Ser Leu Arg Cys
    1685            1690                1695

Gln Val Ser Gly Ser Pro Pro His Tyr Phe Tyr Trp Ser Arg Glu
    1700            1705                1710

Asp Gly Arg Pro Val Pro Ser Gly Thr Gln Gln Arg His Gln Gly
    1715            1720                1725

Ser Glu Leu His Phe Pro Ser Val Gln Pro Ser Asp Ala Gly Val
    1730            1735                1740

Tyr Ile Cys Thr Cys Arg Asn Leu His Gln Ser Asn Thr Ser Arg
    1745            1750                1755

Ala Glu Leu Leu Val Thr Glu Ala Pro Ser Lys Pro Ile Thr Val
    1760            1765                1770

Thr Val Glu Glu Gln Arg Ser Gln Ser Val Arg Pro Gly Ala Asp
    1775            1780                1785

Val Thr Phe Ile Cys Thr Ala Lys Ser Lys Ser Pro Ala Tyr Thr
    1790            1795                1800

Leu Val Trp Thr Arg Leu His Asn Gly Lys Leu Pro Thr Arg Ala
    1805            1810                1815

Met Asp Phe Asn Gly Ile Leu Thr Ile Arg Asn Val Gln Leu Ser
    1820            1825                1830

Asp Ala Gly Thr Tyr Val Cys Thr Gly Ser Asn Met Phe Ala Met
    1835            1840                1845

Asp Gln Gly Thr Ala Thr Leu His Val Gln Ala Ser Gly Thr Leu
    1850            1855                1860

Ser Ala Pro Val Val Ser Ile His Pro Pro Gln Leu Thr Val Gln
    1865            1870                1875
```

-continued

```
Pro Gly Gln Leu Ala Glu Phe Arg Cys Ser Ala Thr Gly Ser Pro
    1880                1885                1890

Thr Pro Thr Leu Glu Trp Thr Gly Gly Pro Gly Gly Gln Leu Pro
    1895                1900                1905

Ala Lys Ala Gln Ile His Gly Gly Ile Leu Arg Leu Pro Ala Val
    1910                1915                1920

Glu Pro Thr Asp Gln Ala Gln Tyr Leu Cys Arg Ala His Ser Ser
    1925                1930                1935

Ala Gly Gln Gln Val Ala Arg Ala Val Leu His Val His Gly Gly
    1940                1945                1950

Gly Gly Pro Arg Val Gln Val Ser Pro Glu Arg Thr Gln Val His
    1955                1960                1965

Ala Gly Arg Thr Val Arg Leu Tyr Cys Arg Ala Ala Gly Val Pro
    1970                1975                1980

Ser Ala Thr Ile Thr Trp Arg Lys Glu Gly Gly Ser Leu Pro Pro
    1985                1990                1995

Gln Ala Arg Ser Glu Arg Thr Asp Ile Ala Thr Leu Leu Ile Pro
    2000                2005                2010

Ala Ile Thr Thr Ala Asp Ala Gly Phe Tyr Leu Cys Val Ala Thr
    2015                2020                2025

Ser Pro Ala Gly Thr Ala Gln Ala Arg Met Gln Val Val Val Leu
    2030                2035                2040

Ser Ala Ser Asp Ala Ser Pro Pro Gly Val Lys Ile Glu Ser Ser
    2045                2050                2055

Ser Pro Ser Val Thr Glu Gly Gln Thr Leu Asp Leu Asn Cys Val
    2060                2065                2070

Val Ala Gly Ser Ala His Ala Gln Val Thr Trp Tyr Arg Arg Gly
    2075                2080                2085

Gly Ser Leu Pro Pro His Thr Gln Val His Gly Ser Arg Leu Arg
    2090                2095                2100

Leu Pro Gln Val Ser Pro Ala Asp Ser Gly Glu Tyr Val Cys Arg
    2105                2110                2115

Val Glu Asn Gly Ser Gly Pro Lys Glu Ala Ser Ile Thr Val Ser
    2120                2125                2130

Val Leu His Gly Thr His Ser Gly Pro Ser Tyr Thr Pro Val Pro
    2135                2140                2145

Gly Ser Thr Arg Pro Ile Arg Ile Glu Pro Ser Ser Ser His Val
    2150                2155                2160

Ala Glu Gly Gln Thr Leu Asp Leu Asn Cys Val Val Pro Gly Gln
    2165                2170                2175

Ala His Ala Gln Val Thr Trp His Lys Arg Gly Gly Ser Leu Pro
    2180                2185                2190

Ala Arg His Gln Thr His Gly Ser Leu Leu Arg Leu His Gln Val
    2195                2200                2205

Thr Pro Ala Asp Ser Gly Glu Tyr Val Cys His Val Val Gly Thr
    2210                2215                2220

Ser Gly Pro Leu Glu Ala Ser Val Leu Val Thr Ile Glu Ala Ser
    2225                2230                2235

Val Ile Pro Gly Pro Ile Pro Pro Val Arg Ile Glu Ser Ser Ser
    2240                2245                2250

Ser Thr Val Ala Glu Gly Gln Thr Leu Asp Leu Ser Cys Val Val
    2255                2260                2265

Ala Gly Gln Ala His Ala Gln Val Thr Trp Tyr Lys Arg Gly Gly
```

-continued

|     |     |     |     |     | 2270 |     |     |     |     | 2275 |     |     |     |     | 2280 |
| --- | --- | --- | --- | --- | ---  | --- | --- | --- | --- | ---  | --- | --- | --- | --- | ---  |
| Ser | Leu | Pro | Ala | Arg | His  | Gln | Val | Arg | Gly | Ser  | Arg | Leu | Tyr | Ile |
|     |     |     |     |     | 2285 |     |     |     |     | 2290 |     |     |     |     | 2295 |
| Phe | Gln | Ala | Ser | Pro | Ala  | Asp | Ala | Gly | Gln | Tyr  | Val | Cys | Arg | Ala |
|     |     |     |     |     | 2300 |     |     |     |     | 2305 |     |     |     |     | 2310 |
| Ser | Asn | Gly | Met | Glu | Ala  | Ser | Ile | Thr | Val | Thr  | Val | Thr | Gly | Thr |
|     |     |     |     |     | 2315 |     |     |     |     | 2320 |     |     |     |     | 2325 |
| Gln | Gly | Ala | Asn | Leu | Ala  | Tyr | Pro | Ala | Gly | Ser  | Thr | Gln | Pro | Ile |
|     |     |     |     |     | 2330 |     |     |     |     | 2335 |     |     |     |     | 2340 |
| Arg | Ile | Glu | Pro | Ser | Ser  | Ser | Gln | Val | Ala | Glu  | Gly | Gln | Thr | Leu |
|     |     |     |     |     | 2345 |     |     |     |     | 2350 |     |     |     |     | 2355 |
| Asp | Leu | Asn | Cys | Val | Val  | Pro | Gly | Gln | Ser | His  | Ala | Gln | Val | Thr |
|     |     |     |     |     | 2360 |     |     |     |     | 2365 |     |     |     |     | 2370 |
| Trp | His | Lys | Arg | Gly | Gly  | Ser | Leu | Pro | Val | Arg  | His | Gln | Thr | His |
|     |     |     |     |     | 2375 |     |     |     |     | 2380 |     |     |     |     | 2385 |
| Gly | Ser | Leu | Leu | Arg | Leu  | Tyr | Gln | Ala | Ser | Pro  | Ala | Asp | Ser | Gly |
|     |     |     |     |     | 2390 |     |     |     |     | 2395 |     |     |     |     | 2400 |
| Glu | Tyr | Val | Cys | Arg | Val  | Leu | Gly | Ser | Ser | Val  | Pro | Leu | Glu | Ala |
|     |     |     |     |     | 2405 |     |     |     |     | 2410 |     |     |     |     | 2415 |
| Ser | Val | Leu | Val | Thr | Ile  | Glu | Pro | Ala | Gly | Ser  | Val | Pro | Ala | Leu |
|     |     |     |     |     | 2420 |     |     |     |     | 2425 |     |     |     |     | 2430 |
| Gly | Val | Thr | Pro | Thr | Val  | Arg | Ile | Glu | Ser | Ser  | Ser | Ser | Gln | Val |
|     |     |     |     |     | 2435 |     |     |     |     | 2440 |     |     |     |     | 2445 |
| Ala | Glu | Gly | Gln | Thr | Leu  | Asp | Leu | Asn | Cys | Leu  | Val | Ala | Gly | Gln |
|     |     |     |     |     | 2450 |     |     |     |     | 2455 |     |     |     |     | 2460 |
| Ala | His | Ala | Gln | Val | Thr  | Trp | His | Lys | Arg | Gly  | Gly | Ser | Leu | Pro |
|     |     |     |     |     | 2465 |     |     |     |     | 2470 |     |     |     |     | 2475 |
| Ala | Arg | His | Gln | Val | His  | Gly | Ser | Arg | Leu | Arg  | Leu | Leu | Gln | Val |
|     |     |     |     |     | 2480 |     |     |     |     | 2485 |     |     |     |     | 2490 |
| Thr | Pro | Ala | Asp | Ser | Gly  | Glu | Tyr | Val | Cys | Arg  | Val | Val | Gly | Ser |
|     |     |     |     |     | 2495 |     |     |     |     | 2500 |     |     |     |     | 2505 |
| Ser | Gly | Thr | Gln | Glu | Ala  | Ser | Val | Leu | Val | Thr  | Ile | Gln | Gln | Arg |
|     |     |     |     |     | 2510 |     |     |     |     | 2515 |     |     |     |     | 2520 |
| Leu | Ser | Gly | Ser | His | Ser  | Gln | Gly | Val | Ala | Tyr  | Pro | Val | Arg | Ile |
|     |     |     |     |     | 2525 |     |     |     |     | 2530 |     |     |     |     | 2535 |
| Glu | Ser | Ser | Ser | Ala | Ser  | Leu | Ala | Asn | Gly | His  | Thr | Leu | Asp | Leu |
|     |     |     |     |     | 2540 |     |     |     |     | 2545 |     |     |     |     | 2550 |
| Asn | Cys | Leu | Val | Ala | Ser  | Gln | Ala | Pro | His | Thr  | Ile | Thr | Trp | Tyr |
|     |     |     |     |     | 2555 |     |     |     |     | 2560 |     |     |     |     | 2565 |
| Lys | Arg | Gly | Gly | Ser | Leu  | Pro | Ser | Arg | His | Gln  | Ile | Val | Gly | Ser |
|     |     |     |     |     | 2570 |     |     |     |     | 2575 |     |     |     |     | 2580 |
| Arg | Leu | Arg | Ile | Pro | Gln  | Val | Thr | Pro | Ala | Asp  | Ser | Gly | Glu | Tyr |
|     |     |     |     |     | 2585 |     |     |     |     | 2590 |     |     |     |     | 2595 |
| Val | Cys | His | Val | Ser | Asn  | Gly | Ala | Gly | Ser | Arg  | Glu | Thr | Ser | Leu |
|     |     |     |     |     | 2600 |     |     |     |     | 2605 |     |     |     |     | 2610 |
| Ile | Val | Thr | Ile | Gln | Gly  | Ser | Gly | Ser | Ser | His  | Val | Pro | Ser | Val |
|     |     |     |     |     | 2615 |     |     |     |     | 2620 |     |     |     |     | 2625 |
| Ser | Pro | Pro | Ile | Arg | Ile  | Glu | Ser | Ser | Ser | Pro  | Thr | Val | Val | Glu |
|     |     |     |     |     | 2630 |     |     |     |     | 2635 |     |     |     |     | 2640 |
| Gly | Gln | Thr | Leu | Asp | Leu  | Asn | Cys | Val | Val | Ala  | Arg | Gln | Pro | Gln |
|     |     |     |     |     | 2645 |     |     |     |     | 2650 |     |     |     |     | 2655 |
| Ala | Ile | Ile | Thr | Trp | Tyr  | Lys | Arg | Gly | Gly | Ser  | Leu | Pro | Ser | Arg |
|     |     |     |     |     | 2660 |     |     |     |     | 2665 |     |     |     |     | 2670 |

-continued

```
His Gln Thr His Gly Ser His Leu Arg Leu His Gln Met Ser Val
2675                2680                2685

Ala Asp Ser Gly Glu Tyr Val Cys Arg Ala Asn Asn Asn Ile Asp
2690                2695                2700

Ala Leu Glu Ala Ser Ile Val Ile Ser Val Ser Pro Ser Ala Gly
2705                2710                2715

Ser Pro Ser Ala Pro Gly Ser Ser Met Pro Ile Arg Ile Glu Ser
2720                2725                2730

Ser Ser Ser His Val Ala Glu Gly Glu Thr Leu Asp Leu Asn Cys
2735                2740                2745

Val Val Pro Gly Gln Ala His Ala Gln Val Thr Trp His Lys Arg
2750                2755                2760

Gly Gly Ser Leu Pro Ser His His Gln Thr Arg Gly Ser Arg Leu
2765                2770                2775

Arg Leu His His Val Ser Pro Ala Asp Ser Gly Glu Tyr Val Cys
2780                2785                2790

Arg Val Met Gly Ser Ser Gly Pro Leu Glu Ala Ser Val Leu Val
2795                2800                2805

Thr Ile Glu Ala Ser Gly Ser Ser Ala Val His Val Pro Ala Pro
2810                2815                2820

Gly Gly Ala Pro Pro Ile Arg Ile Glu Pro Ser Ser Ser Arg Val
2825                2830                2835

Ala Glu Gly Gln Thr Leu Asp Leu Lys Cys Val Val Pro Gly Gln
2840                2845                2850

Ala His Ala Gln Val Thr Trp His Lys Arg Gly Gly Asn Leu Pro
2855                2860                2865

Ala Arg His Gln Val His Gly Pro Leu Leu Arg Leu Asn Gln Val
2870                2875                2880

Ser Pro Ala Asp Ser Gly Glu Tyr Ser Cys Gln Val Thr Gly Ser
2885                2890                2895

Ser Gly Thr Leu Glu Ala Ser Val Leu Val Thr Ile Glu Pro Ser
2900                2905                2910

Ser Pro Gly Pro Ile Pro Ala Pro Gly Leu Ala Gln Pro Ile Tyr
2915                2920                2925

Ile Glu Ala Ser Ser Ser His Val Thr Glu Gly Gln Thr Leu Asp
2930                2935                2940

Leu Asn Cys Val Val Pro Gly Gln Ala His Ala Gln Val Thr Trp
2945                2950                2955

Tyr Lys Arg Gly Gly Ser Leu Pro Ala Arg His Gln Thr His Gly
2960                2965                2970

Ser Gln Leu Arg Leu His Leu Val Ser Pro Ala Asp Ser Gly Glu
2975                2980                2985

Tyr Val Cys Arg Ala Ala Ser Gly Pro Gly Pro Glu Gln Glu Ala
2990                2995                3000

Ser Phe Thr Val Thr Val Pro Pro Ser Glu Gly Ser Ser Tyr Arg
3005                3010                3015

Leu Arg Ser Pro Val Ile Ser Ile Asp Pro Pro Ser Ser Thr Val
3020                3025                3030

Gln Gln Gly Gln Asp Ala Ser Phe Lys Cys Leu Ile His Asp Gly
3035                3040                3045

Ala Ala Pro Ile Ser Leu Glu Trp Lys Thr Arg Asn Gln Glu Leu
3050                3055                3060
```

-continued

| | | | | | | | | | | |
|---|---|---|---|---|---|---|---|---|---|---|
| Glu | Asp | Asn | Val | His | Ile | Ser | Pro | Asn | Gly | Ser | Ile | Ile | Thr | Ile |
| 3065 | | | | 3070 | | | | 3075 | | |

Val Gly Thr Arg Pro Ser Asn His Gly Thr Tyr Arg Cys Val Ala
3080              3085              3090

Ser Asn Ala Tyr Gly Val Ala Gln Ser Val Val Asn Leu Ser Val
3095              3100              3105

His Gly Pro Pro Thr Val Ser Val Leu Pro Glu Gly Pro Val Trp
3110              3115              3120

Val Lys Val Gly Lys Ala Val Thr Leu Glu Cys Val Ser Ala Gly
3125              3130              3135

Glu Pro Arg Ser Ser Ala Arg Trp Thr Arg Ile Ser Ser Thr Pro
3140              3145              3150

Ala Lys Leu Glu Gln Arg Thr Tyr Gly Leu Met Asp Ser His Ala
3155              3160              3165

Val Leu Gln Ile Ser Ser Ala Lys Pro Ser Asp Ala Gly Thr Tyr
3170              3175              3180

Val Cys Leu Ala Gln Asn Ala Leu Gly Thr Ala Gln Lys Gln Val
3185              3190              3195

Glu Val Ile Val Asp Thr Gly Ala Met Ala Pro Gly Ala Pro Gln
3200              3205              3210

Val Gln Ala Glu Glu Ala Glu Leu Thr Val Glu Ala Gly His Thr
3215              3220              3225

Ala Thr Leu Arg Cys Ser Ala Thr Gly Ser Pro Ala Pro Thr Ile
3230              3235              3240

His Trp Ser Lys Leu Arg Ser Pro Leu Pro Trp Gln His Arg Leu
3245              3250              3255

Glu Gly Asp Thr Leu Ile Ile Pro Arg Val Ala Gln Gln Asp Ser
3260              3265              3270

Gly Gln Tyr Ile Cys Asn Ala Thr Ser Pro Ala Gly His Ala Glu
3275              3280              3285

Ala Thr Ile Ile Leu His Val Glu Ser Pro Pro Tyr Ala Thr Thr
3290              3295              3300

Val Pro Glu His Ala Ser Val Gln Ala Gly Glu Thr Val Gln Leu
3305              3310              3315

Gln Cys Leu Ala His Gly Thr Pro Pro Leu Thr Phe Gln Trp Ser
3320              3325              3330

Arg Val Gly Ser Ser Leu Pro Gly Arg Ala Thr Ala Arg Asn Glu
3335              3340              3345

Leu Leu His Phe Glu Arg Ala Ala Pro Glu Asp Ser Gly Arg Tyr
3350              3355              3360

Arg Cys Arg Val Thr Asn Lys Val Gly Ser Ala Glu Ala Phe Ala
3365              3370              3375

Gln Leu Leu Val Gln Gly Pro Pro Gly Ser Leu Pro Ala Thr Ser
3380              3385              3390

Ile Pro Ala Gly Ser Thr Pro Thr Val Gln Val Thr Pro Gln Leu
3395              3400              3405

Glu Thr Lys Ser Ile Gly Ala Ser Val Glu Phe His Cys Ala Val
3410              3415              3420

Pro Ser Asp Gln Gly Thr Gln Leu Arg Trp Phe Lys Glu Gly Gly
3425              3430              3435

Gln Leu Pro Pro Gly His Ser Val Gln Asp Gly Val Leu Arg Ile
3440              3445              3450

Gln Asn Leu Asp Gln Ser Cys Gln Gly Thr Tyr Ile Cys Gln Ala

|  |  |  |
|---|---|---|
| 3455 | 3460 | 3465 |

His Gly Pro Trp Gly Lys Ala Gln Ala Ser Ala Gln Leu Val Ile
          3470                          3475                        3480

Gln Ala Leu Pro Ser Val Leu Ile Asn Ile Arg Thr Ser Val Gln
          3485                          3490                        3495

Thr Val Val Val Gly His Ala Val Glu Phe Glu Cys Leu Ala Leu
          3500                          3505                        3510

Gly Asp Pro Lys Pro Gln Val Thr Trp Ser Lys Val Gly Gly His
          3515                          3520                        3525

Leu Arg Pro Gly Ile Val Gln Ser Gly Gly Val Val Arg Ile Ala
          3530                          3535                        3540

His Val Glu Leu Ala Asp Ala Gly Gln Tyr Arg Cys Thr Ala Thr
          3545                          3550                        3555

Asn Ala Ala Gly Thr Thr Gln Ser His Val Leu Leu Leu Val Gln
          3560                          3565                        3570

Ala Leu Pro Gln Ile Ser Met Pro Gln Glu Val Arg Val Pro Ala
          3575                          3580                        3585

Gly Ser Ala Ala Val Phe Pro Cys Ile Ala Ser Gly Tyr Pro Thr
          3590                          3595                        3600

Pro Asp Ile Ser Trp Ser Lys Leu Asp Gly Ser Leu Pro Pro Asp
          3605                          3610                        3615

Ser Arg Leu Glu Asn Asn Met Leu Met Leu Pro Ser Val Arg Pro
          3620                          3625                        3630

Gln Asp Ala Gly Thr Tyr Val Cys Thr Ala Thr Asn Arg Gln Gly
          3635                          3640                        3645

Lys Val Lys Ala Phe Ala His Leu Gln Val Pro Glu Arg Val Val
          3650                          3655                        3660

Pro Tyr Phe Thr Gln Thr Pro Tyr Ser Phe Leu Pro Leu Pro Thr
          3665                          3670                        3675

Ile Lys Asp Ala Tyr Arg Lys Phe Glu Ile Lys Ile Thr Phe Arg
          3680                          3685                        3690

Pro Asp Ser Ala Asp Gly Met Leu Leu Tyr Asn Gly Gln Lys Arg
          3695                          3700                        3705

Val Pro Gly Ser Pro Thr Asn Leu Ala Asn Arg Gln Pro Asp Phe
          3710                          3715                        3720

Ile Ser Phe Gly Leu Val Gly Gly Arg Pro Glu Phe Arg Phe Asp
          3725                          3730                        3735

Ala Gly Ser Gly Met Ala Thr Ile Arg His Pro Thr Pro Leu Ala
          3740                          3745                        3750

Leu Gly His Phe His Thr Val Thr Leu Leu Arg Ser Leu Thr Gln
          3755                          3760                        3765

Gly Ser Leu Ile Val Gly Asp Leu Ala Pro Val Asn Gly Thr Ser
          3770                          3775                        3780

Gln Gly Lys Phe Gln Gly Leu Asp Leu Asn Glu Glu Leu Tyr Leu
          3785                          3790                        3795

Gly Gly Tyr Pro Asp Tyr Gly Ala Ile Pro Lys Ala Gly Leu Ser
          3800                          3805                        3810

Ser Gly Phe Ile Gly Cys Val Arg Glu Leu Arg Ile Gln Gly Glu
          3815                          3820                        3825

Glu Ile Val Phe His Asp Leu Asn Leu Thr Ala His Gly Ile Ser
          3830                          3835                        3840

His Cys Pro Thr Cys Arg Asp Arg Pro Cys Gln Asn Gly Gly Gln
          3845                          3850                        3855

-continued

```
Cys His Asp Ser Glu Ser Ser Tyr Val Cys Val Cys Pro Ala
3860           3865           3870

Gly Phe Thr Gly Ser Arg Cys Glu His Ser Gln Ala Leu His Cys
3875           3880           3885

His Pro Glu Ala Cys Gly Pro Asp Ala Thr Cys Val Asn Arg Pro
3890           3895           3900

Asp Gly Arg Gly Tyr Thr Cys Arg Cys His Leu Gly Arg Ser Gly
3905           3910           3915

Leu Arg Cys Glu Glu Gly Val Thr Val Thr Thr Pro Ser Leu Ser
3920           3925           3930

Gly Ala Gly Ser Tyr Leu Ala Leu Pro Ala Leu Thr Asn Thr His
3935           3940           3945

His Glu Leu Arg Leu Asp Val Glu Phe Lys Pro Leu Ala Pro Asp
3950           3955           3960

Gly Val Leu Leu Phe Ser Gly Gly Lys Ser Gly Pro Val Glu Asp
3965           3970           3975

Phe Val Ser Leu Ala Met Val Gly Gly His Leu Glu Phe Arg Tyr
3980           3985           3990

Glu Leu Gly Ser Gly Leu Ala Val Leu Arg Ser Ala Glu Pro Leu
3995           4000           4005

Ala Leu Gly Arg Trp His Arg Val Ser Ala Glu Arg Leu Asn Lys
4010           4015           4020

Asp Gly Ser Leu Arg Val Asn Gly Gly Arg Pro Val Leu Arg Ser
4025           4030           4035

Ser Pro Gly Lys Ser Gln Gly Leu Asn Leu His Thr Leu Leu Tyr
4040           4045           4050

Leu Gly Gly Val Glu Pro Ser Val Pro Leu Ser Pro Ala Thr Asn
4055           4060           4065

Met Ser Ala His Phe Arg Gly Cys Val Gly Glu Val Ser Val Asn
4070           4075           4080

Gly Lys Arg Leu Asp Leu Thr Tyr Ser Phe Leu Gly Ser Gln Gly
4085           4090           4095

Ile Gly Gln Cys Tyr Asp Ser Ser Pro Cys Glu Arg Gln Pro Cys
4100           4105           4110

Gln His Gly Ala Thr Cys Met Pro Ala Gly Glu Tyr Glu Phe Gln
4115           4120           4125

Cys Leu Cys Arg Asp Gly Phe Lys Gly Asp Leu Cys Glu His Glu
4130           4135           4140

Glu Asn Pro Cys Gln Leu Arg Glu Pro Cys Leu His Gly Gly Thr
4145           4150           4155

Cys Gln Gly Thr Arg Cys Leu Cys Leu Pro Gly Phe Ser Gly Pro
4160           4165           4170

Arg Cys Gln Gln Gly Ser Gly His Gly Ile Ala Glu Ser Asp Trp
4175           4180           4185

His Leu Glu Gly Ser Gly Gly Asn Asp Ala Pro Gly Gln Tyr Gly
4190           4195           4200

Ala Tyr Phe His Asp Asp Gly Phe Leu Ala Phe Pro Gly His Val
4205           4210           4215

Phe Ser Arg Ser Leu Pro Glu Val Pro Glu Thr Ile Glu Leu Glu
4220           4225           4230

Val Arg Thr Ser Thr Ala Ser Gly Leu Leu Leu Trp Gln Gly Val
4235           4240           4245
```

```
Glu Val Gly Glu Ala Gly Gln Gly Lys Asp Phe Ile Ser Leu Gly
    4250            4255                4260
Leu Gln Asp Gly His Leu Val Phe Arg Tyr Gln Leu Gly Ser Gly
    4265            4270                4275
Glu Ala Arg Leu Val Ser Glu Asp Pro Ile Asn Asp Gly Glu Trp
    4280            4285                4290
His Arg Val Thr Ala Leu Arg Glu Gly Arg Gly Ser Ile Gln
    4295            4300                4305
Val Asp Gly Glu Glu Leu Val Ser Gly Arg Ser Pro Gly Pro Asn
    4310            4315                4320
Val Ala Val Asn Ala Lys Gly Ser Val Tyr Ile Gly Gly Ala Pro
    4325            4330                4335
Asp Val Ala Thr Leu Thr Gly Gly Arg Phe Ser Ser Gly Ile Thr
    4340            4345                4350
Gly Cys Val Lys Asn Leu Val Leu His Ser Ala Arg Pro Gly Ala
    4355            4360                4365
Pro Pro Pro Gln Pro Leu Asp Leu Gln His Arg Ala Gln Ala Gly
    4370            4375                4380
Ala Asn Thr Arg Pro Cys Pro Ser
    4385            4390

<210> SEQ ID NO 5
<211> LENGTH: 14327
<212> TYPE: DNA
<213> ORGANISM: Homo sapiens

<400> SEQUENCE: 5
ggccggcgag cgggcggctg cgggcggcgc ggagcgggcg cgcggagcg agcgagcgag        60 agagcggcgc gggccgggcc atggggtggc gggcgccggg cgcgctgctg ctggcgctgc      120
tgctgcacgg gcggctgctg gcggtgaccc atgggctgag gcatacgat ggcttgtctc       180 tgcctgagga catagagacc gtcacagcaa gccaaatgcg ctggacacat tcgtaccttt      240
ctgatgatga gtacatgctg gctgacagca tctcaggaga cgacctgggc agtggggacc      300
tgggcagcgg ggacttccag atggtttatt tccgagccct ggtgaatttc actcgctcca      360
tcgagtacag ccctcagctg gaggatgcag gctccagaga gtttcgagag gtgtccgagg      420
ctgtggtaga cacgctggag tcggagtact tgaaaattcc cggagaccag gttgtcagtg      480
tggtgttcat caaggagctg gatggctggg ttttgtgga gctcgatgtg ggctcggaag       540
ggaatgcgga tggtgctcag attcaggaga tgctgctcag ggtcatctcc agcggctctg     600
tggcctccta cgtcacctct ccccagggat tccagttccg acgcctgggc acagtgcccc      660
agttcccaag agcctgcacg gaggccgagt ttgcctgcca cagctacaat gagtgtgtgg      720
ccctggagta tcgctgtgac cggcggcccg actgcaggga catgtctgat gagctcaatt      780
gtgaggagcc agtcctgggt atcagcccca cattctctct ccttgtggag acgacatctt      840
taccgccccg ccagagacac accatcatgc gacagccacc agtcacccac gctcctcagc      900
ccctgcttcc cggttccgtc aggccctgc cctgtgggcc ccaggaggcc gcatgccgca      960
atgggcactg catccccaga gactacctct gcgacggaca ggaggactgc gaggacggca     1020
gcgatgagct agactgtggc ccccgccac cctgtgagcc caacgagttc ccctgcggga     1080
atggacattg tgccctcaag ctgtggcgct gcgatggtga ctttgactgt gaggaccgaa     1140
ctgatgaagc caactgcccc accaagcgtc tgaggaagt gtgcgggccc acacagttcc     1200
gatgcgtctc taccaacatg tgcatcccag ccagcttcca ctgtgacgag gagagcgact     1260
```

-continued

```
gtcctgaccg gagcgacgag tttggctgca tgccccccca ggtggtgaca cctccccggg    1320
agtccatcca ggcttccggg gccagacagt gaccttcac ctgcgtggcc attggcgtcc    1380
ccaccccat catcaattgg aggctcaact ggggccacat cccctctcat cccagggtga    1440
cagtgaccag cgagggtggc cgtggcacac tgatcatccg tgatgtgaag gagtcagacc    1500
agggtgccta cacctgtgag gccatgaacg cccggggcat ggtgtttggc attcctgacg    1560
gtgtccttga gctcgtccca caacgaggcc cctgccctga cggccacttc tacctggagc    1620
acagcgccgc ctgcctgccc tgcttctgct ttggcatcac cagcgtgtgc cagagcaccc    1680
gccgcttccg ggaccagatc aggctgcgct tgaccaacc cgatgacttc aagggtgtga    1740
atgtgacaat gcctgcgcag cccggcacgc caccctctc ctccacgcag ctgcagatcg    1800
acccatccct gcacgagttc cagctagtag acctgtcccg ccgcttcctc gtccacgact    1860
ccttctgggc tctgcctgaa cagttcctgg caacaaggt ggactcctat ggcggctccc    1920
tgcgttacaa cgtgcgctac gagttggccc gtggcatgct ggagccagtg cagcggccgg    1980
acgtggtcct cgtgggtgcc gggtaccgcc tcctctcccg aggccacaca cccacccaac    2040
ctggtgctct gaaccagcgc caggtccagt tctctgagga gcactgggtc catgagtctg    2100
gccggccggt gcagcgcgcg gagctgctgc aggtgctgca gagcctggag gccgtgctca    2160
tccagaccgt gtacaacacc aagatggcta gcgtgggact agcgacatc gccatggata    2220
ccaccgtcac ccatgccacc agccatggcc gtgcccacag tgtggaggag tgcagatgcc    2280
ccattggcta ttctggcttg tcctgcgaga gctgtgatgc ccacttcact cgggtgcctg    2340
gtgggcccta cctgggcacc tgctctggtt gcagttgcaa tggccatgcc agctcctgtg    2400
accctgtgta tggccactgc ctgaattgcc agcacaacac ggaggggcca cagtgcaaca    2460
agtgcaaggc tggcttcttt ggggacgcca tgaaggccac ggccacttcc tgccggccct    2520
gcccttgccc atacatcgat gcctcccgca gattctcaga cacttgcttc ctggacacgg    2580
atggccaagc cacatgtgac gcctgtgccc caggctacac tggccgccgc tgtgagagct    2640
gtgccccgg atacgagggc aaccccatcc agccggcgg gaagtgcagg cccgtcaacc    2700
aggagattgt gcgctgtgac gagcgtggca gcatgggac ctccggggag gcctgccgct    2760
gtaagaacaa tgtggtgggg cgcttgtgca atgaatgtgc tgacggctct ttccacctga    2820
gtacccgaaa ccccgatggc tgcctcaagt gcttctgcat gggtgtcagt cgccactgca    2880
ccagctcttc atggagccgt gcccagttgc atggggcctc tgaggagcct ggtcacttca    2940
gcctgaccaa cgccgcaagc acccacacca caacgaggg catcttctcc cccacgcccg    3000
gggaactggg attctcctcc ttccacagac tcttatctgg accctacttc tggagcctcc    3060
cttcacgctt cctggggggac aaggtgacct cctatggagg agagctgcgc ttcacagtga    3120
cccagaggtc ccagccgggc tccacacccc tgcacgggca gccgttggtg gtgctgcaag    3180
gtaacaacat catcctagag caccatgtgg cccaggagcc cagccccggc cagcccagca    3240
ccttcattgt gccttttccgg gagcaagcat ggcagcggcc cgatgggcag ccagccacac    3300
gggagcacct gctgatggca ctggcaggca tcgacaccct cctgatccga gcatcctacg    3360
cccagcagcc cgctgagagc agggtctctg gcatcagcat ggacgtggct gtgcccgagg    3420
aaaccggcca ggaccccgcg ctggaagtgg aacagtgctc ctgcccaccc gggtaccgtg    3480
ggccgtcctg ccaggactgt gacacaggct acacacgcac gcccagtggc ctctacctgg    3540
gtacctgtga acgctgcagc tgccatggcc actcagaggc ctgcgagcca gaaacaggtg    3600
```

-continued

```
cctgccaggg ctgccagcat cacacggagg gccctcggtg tgagcagtgc cagccaggat    3660 actacggga  cgcccagcgg gggacaccac aggactgcca gctgtgcccc tgctacggag    3720
accctgctgc cggccaggct gcccacactt gttttctgga cacagacggc cacccacct    3780 gtgatgcgtg ctccccaggc cacagtgggc gtcactgtga gaggtgcgcc cctggctact    3840
atggcaaccc cagccagggc cagccatgcc agagagacag ccaggtgcca gggcccatag    3900
gctgcaactg tgaccccaa  ggcagcgtca gcagccagtg tgatgctgct ggtcagtgcc    3960
agtgcaaggc ccaggtagaa ggcctcactt gcagccactg ccggccccac cacttccacc    4020
tgagtgccag caacccagac ggctgcctgc cctgcttctg tatgggcatc acccagcagt    4080
gcgccagctc tgcctacaca cgccacctga tctccaccca ctttgcccct ggggacttcc    4140
aaggctttgc cctggtgaac ccacagcgaa acagccgcct gacaggagaa ttcactgtgg    4200
aacccgtgcc cgagggtgcc cagctctctt ttggcaactt tgcccaactc ggccatgagt    4260
ccttctactg gcagctgccg gagacatacc agggagacaa ggtggcggcc tacgtggga    4320 agttgcgata caccctctcc tacacagcag gcccacaggg cagcccactc tcggaccccg    4380
atgtgcagat cacgggcaac aacatcatgc tagtggcctc ccagcagcg  ctgcagggcc    4440 cagagaggag gagctacgag atcatgttcc gagaggaatt ctggcgccgg cccgatgggc    4500
agccggccac acgcgagcac ctcctgatgg cactggccga cctggatgag ctcctgatcc    4560
gggccacgtt ctcctccgtg ccgctggtgg ccagcatcag cgcagtcagc ctggaggtcg    4620
cccagccggg gccctcaaac agaccccgcg ccctcgaggt ggaggagtgc cgctgcccgc    4680
caggctacat cggtctgtcc tgccaggact gtgcccccgg ctacacgcgc accgggagtg    4740
ggctctacct cggccactgc gagctatgtg aatgcaatgg ccactcagac ctgtgccacc    4800
cagagactgg ggcctgctcg caatgccagc acaacgccgc aggggagttc tgcgagcttt    4860
gtgcccctgg ctactacgga gatgccacag ccgggacgcc tgaggactgc agccctgtg    4920 cctgcccact gaccaaccca gagaacatgt tttcccgcac ctgtgagagc ctgggagccg    4980
gcgggtaccg ctgcacggcc tgcgaacccg gctacactgg ccagtactgt gagcagtgtg    5040
gcccaggtta cgtgggtaac cccagtgtgc aaggggggcca gtgcctgcca gagacaaacc    5100
aagccccact ggtggtcgag gtccatcctg ctcgaagcat agtgcccaa  ggtggctccc    5160 actccctgcg gtgtcaggtc agtgggagcc caccccacta cttctattgg tcccgtgagg    5220
atgggcggcc tgtgcccagc ggcacccagc agcgacatca aggctccgag ctccacttcc    5280
ccagcgtcca gccctcggat gctgggggtct acatttgcac ctgccgtaat ctccaccaat    5340
ccaataccag ccgggcagag ctgctggtca ctgaggctcc aagcaagccc atcacagtga    5400
ctgtggagga gcagcggagc cagagcgtgc gccccgagc  tgacgtcacc ttcatctgca    5460
cagccaaaag caagtcccca gcctataccc tggtgtggac ccgcctgcac aacgggaaac    5520
tgcccacccg agccatggat ttcaatggca tcctgaccat tcgcaacgtc cagctgagtg    5580
atgcaggcac ctacgtgtgc accggctcca acatgtttgc catggaccag ggcacagcca    5640
ctctacatgt gcaggcctcg ggcaccttgt ccgccccgt  ggtctccatc catccgccac    5700
agctcacagt gcagcccggg caactggcgg agttccgctg cagcgccaca gggagcccca    5760
cgcccaccct cgagtggaca gggggccccg gcggccagct ccctgcgaag gcacaaatcc    5820
acggcggcat cctgcgcctg ccagctgtcg agcccacgga tcaggcccag tacttgtgcc    5880
gagcccacag cagcgctggg cagcaggtgg ccagggctgt gctccacgtg catggggcg    5940 gtgggcccag agtccaagtg agcccagaga ggacccaggt ccacgcaggc cggaccgtca    6000
```

```
ggctgtactg cagggctgca ggcgtgccta gcgccaccat cacctggagg aaggaagggg     6060
gcagcctccc accacaggcc cggtcagagc gcacagacat cgcgacactg ctcatcccag     6120
ccatcacgac tgctgacgcc ggcttctacc tctgcgtggc caccagccct gcaggcactg     6180
cccaggcccg gatgcaagtg gttgtccttt cagcctcaga tgccagccca ccggggtca      6240 agattgagtc ctcatcgcct tctgtgacag aagggcaaac actcgacctc aactgtgtgg     6300
tggcagggtc agcccatgcc caggtcacct ggtacaggcg aggggtagc ctgcctcccc      6360 acacccaggt gcacggctcc cgtctgcggc tccccaggt ctcaccagct gattctggag       6420
aatatgtgtg ccgtgtggag aatggatcgg gccccaagga ggcctccatt actgtgtctg     6480
tgctccacgg cacccattct ggccccagct acacccagt gcccggcagc acccggccca      6540
tccgcatcga gccctcctcc tcacacgtgg cggaagggca gaccctggat ctgaactgcg     6600
tggtgcccgg gcaggcccac gcccaggtca cgtggcacaa gcgtgggggc agcctccctg     6660
cccggcacca gacccacggc tcgctgctgc ggctgcacca ggtgaccccg gccgactcag     6720
gcgagtatgt gtgccatgtg gtgggcacct ccggcccct agaggcctca gtcctggtca      6780
ccatcgaagc ctctgtcatc cctggaccca tcccacctgt caggatcgag tcttcatcct     6840
ccacagtggc cgagggccag accctggatc tgagctgcgt ggtggcaggg caggcccacg     6900
cccaggtcac atggtacaag cgtgggggca gcctccctgc ccggcaccag gttcgtggct     6960
cccgcctgta catcttccag gcctcacctg ccgatgcggg acagtacgtc tgccgggcca    7020
gcaacggcat ggaggcctcc atcacggtca cagtaactgg gacccagggg ccaacttag      7080 cctaccctgc cggcagcacc cagcccatcc gcatcgagcc ctcctcctcg caagtggcgg     7140
aagggcagac cctggatctg aactgcgtgg tgcccgggca gtcccatgcc caggtcacgt     7200
ggcacaagcg tgggggcagc ctccctgtcc ggcaccagac ccacggctcc ctgctgagac     7260
tctaccaagc gtcccccgcc gactcgggcg agtacgtgtg ccgagtgttg ggcagctccg     7320
tgcctctaga ggcctctgtc ctggtcacca ttgagcctgc gggctcagtg cctgcacttg     7380
gggtcacccc cacggtccgg atcgagtcat cgtcttcgca agtggccgag ggcagaccc      7440 tggacctgaa ctgcctcgtt gctggtcagg ccatgccca ggtcacgtgg cacaagcgcg      7500
ggggcagcct cccggcccgg caccaggtgc atggctcgag gctacgcctg ctccaggtga     7560
ccccagctga ttcaggggag tacgtgtgcc gtgtggtcgg cagctcaggt acccaggaag     7620
cctcagtcct tgtcaccatc cagcagcgcc ttagtggctc ccactcccag ggtgtggcgt     7680
accccgtccg catcgagtcc tcctcagcct ccctggccaa tggacacacc ctggacctca    7740
actgcctggt tgccagccag gctccccaca ccatcacctg gtataagcgt ggaggcagct     7800
tacccagccg gcaccagatc gtgggctccc ggctgcggat ccctcaggtg actccggcag     7860
actcgggcga gtacgtgtgt cacgtcagta acggtgcagg ctcccgggag acctcgctca     7920
tcgtcaccat ccagggcagc ggttcctccc acgtgccag cgtctcccca ccgatcagga      7980
tcgagtcgtc ttcccccacg gtggtggaag gcagaccttg gatctgaac tgcgtggtcg      8040 ccaggcagcc ccaggctatc atcacatggt acaagcgtgg gggcagcctt ccctcccgac     8100
accagaccca tggctcccac ctgcggttgc accaaatgtc tgtggctgac tcgggcgagt     8160
atgtgtgccg ggccaacaac aacatcgatg ccctggaggc ctccatcgtc atctccgtct     8220 ccctagcgc cggcagcccc tccgcccctg gcagctccat gcccatcaga attgagtcat      8280
cctcctcaca cgtggccgaa ggggagaccc tggatctgaa ctgcgtggtc cccgggcagg    8340
```

```
cccatgccca ggtcacttgg cacaagcgtg ggggcagcct ccccagtcac catcagaccc   8400
gcggctcacg gctgcggctg caccatgtgt ccccggccga ctcgggtgaa tacgtgtgcc   8460
gggtgatggg cagctctggc cccctggagg cctcagtcct ggtcaccatc gaagcctctg   8520
gctcaagtgc tgtccacgtc cccgcccag gtggagcccc acccatccgc atcgagccct   8580
cctcctcccg agtggcagaa gggcagaccc tggatctgaa gtgcgtggtg cccgggcagg   8640
cccacgccca ggtcacatgg cacaagcgtg gaggaaacct ccctgcccgg caccaggtcc   8700
acggcccact gctgaggctg aaccaggtgt ccccggctga ctctggcgag tactcgtgcc   8760
aagtgaccgg aagctcaggc accctggagg catctgtcct ggtcacaatt gagccctcca   8820
gcccaggacc cattcctgct ccaggactgg cccagcccat ctacatcgag gcctcctctt   8880
cacacgtgac tgaagggcag actctggatc tgaactgtgt ggtgcccggg caggcccatg   8940
cccaggtcac gtggtacaag cgcgggggca gcctccccgc ccggcaccag acccatggct   9000
cccagctgcg gctccacctc gtctcccctg ccgactcagg cgagtatgtg tgtcgtgcag   9060
ccagcggccc aggccctgag caagaagcct ccttcacagt caccgtcccg cccagtgagg   9120
ggtcttccta ccgccttagg agcccggtca tctccatcga cccgcccagc agcaccgtgc   9180
agcagggcca ggatgccagc ttcaagtgcc tcatccatga cggggcagcc cccatcagcc   9240
tcgagtggaa gacccggaac caggagctgg aggacaacgt ccacatcagt cccaatggct   9300
ccatcatcac catcgtgggc acccggccca gcaaccacgg tacctaccgc tgcgtggcct   9360
ccaatgccta cggtgtggcc cagagtgtgg tgaacctcag tgtgcacggg cccctacag   9420 tgtccgtgct ccccgagggc cccgtgtggg tgaaagtggg aaaggctgtc accctggagt   9480
gtgtcagtgc cggggagccc cgctcctctg ctcgttggac ccggatcagc agcacccctg   9540
ccaagttgga gcagcggaca tatgggctca tggacagcca cgcggtgctg cagatttcat   9600
cagctaaacc atcagatgcg ggcacttatg tgtgccttgc tcagaatgca ctaggcacag   9660
cacagaagca ggtggaggtg atcgtggaca cgggcgccat ggccccaggg gcccctcagg   9720
tccaagctga agaagctgag ctgactgtgg aggctggaca cacggccacc ttgcgctgct   9780
cagccacagg cagccccgcg cccaccatcc actggtccaa gctgcgttcc ccactgccct   9840
ggcagcaccg gctggaaggt gacacactca tcatacccg ggtagcccag caggactcgg   9900
gccagtacat ctgcaatgcc actagccctg ctgggcacgc tgaggccacc atcatcctgc   9960
acgtggagag cccaccatat gccaccacgg tcccagagca cgcttcggtg caggcagggg  10020
agacggtgca gctccagtgc ctggctcacg gacaccccc actcaccttc cagtggagcc  10080
gcgtgggcag cagccttcct gggagggcga ccgccaggaa cgagctgctg cactttgagc  10140
gtgcagcccc tgaggactca ggccgctacc gctgccgggt caccaacaag gtgggctcag  10200
ccgaggcctt tgcccagctg ctcgtccaag ccctcccgg ctctctccct gccacctcca  10260
tcccagcagg gtccacgccc accgtgcagg tcacgcctca gctagagacc aagagcattg  10320
gggccagcgt tgagttccac tgtgctgtgc ccagcgacca gggtacccag ctccgttggt  10380
tcaaggaagg gggtcagctg cctccgggtc acagcgtgca ggatggggtg ctccgaatcc  10440
agaacttgga ccagagctgc caagggacgt atatatgcca ggcccatgga ccttggggga  10500
aggcccaggc cagtgcccag ctggttatc aagccctgcc ctcggtgctc atcaacatcc  10560
ggacctctgt gcagaccgtg gtggttggcc acgccgtgga gttcgaatgc ctggcactgg  10620
gtgaccccaa gctcaggtg acatggagca aagttggagg gcacctgcgg ccaggcattg  10680
tgcagagcgg aggtgtcgtc aggatcgccc acgtagagct ggctgatgcg ggacagtatc  10740
```

-continued

```
gctgcactgc caccaacgca gctggcacca cacaatccca cgtcctgctg cttgtgcaag    10800
ccttgcccca gatctcaatg ccccaagaag tccgtgtgcc tgctggttct gcagctgtct    10860
tcccctgcat agcctcaggc taccccactc ctgacatcag ctggagcaag ctggatggca    10920
gcctgccacc tgacagccgc ctggagaaca acatgctgat gctgccctca gtccgacccc    10980
aggacgcagg tacctacgtc tgcaccgcca ctaaccgcca gggcaaggtc aaagcctttg    11040
cccacctgca ggtgccagag cgggtggtgc cctacttcac gcagaccccc tactccttcc    11100
taccgctgcc caccatcaag gatgcctaca ggaagttcga gatcaagatc accttccggc    11160
ccgactcagc cgatgggatg ctgctgtaca atgggcagaa gcgagtccca gggagcccca    11220
ccaacctggc caaccggcag cccgacttca tctccttcgg cctcgtgggg ggaaggcccg    11280
agttccggtt cgatgcaggc tcaggcatgg ccaccatccg ccatcccaca ccactggccc    11340
tgggccattt ccacaccgtg accctgctgc gcagcctcac ccagggctcc ctgattgtgg    11400
gtgacctggc cccggtcaat gggacctccc agggcaagtt ccagggcctg gatctgaacg    11460
aggaactcta cctgggtggc tatcctgact atggtgccat ccccaaggcg gggctgagca    11520
gcggcttcat aggctgtgtc cgggagctgc gcatccaggg cgaggagatc gtcttccatg    11580
acctcaaccct cacggcgcac ggcatctccc actgccccac ctgtcgggac cggccctgcc    11640
agaatggcgg tcagtgccat gactctgaga gcagcagcta cgtgtgcgtc tgcccagctg    11700
gcttcaccgg gagccgctgt gagcactcgc aggccctgca ctgccatcca gaggcctgtg    11760
ggcccgacgc cacctgtgtg aaccggcctg acggtcgagg ctacacctgc cgctgccacc    11820
tgggccgctc ggggttgcgg tgtgaggaag gtgtgacagt gaccaccccc tcgctgtcgg    11880
gtgctggctc ctacctggca ctgcccgccc tcaccaacac acaccacgag ctacgcctgg    11940
acgtggagtt caagccactc gcccctgacg gggtcctgct gttcagcggg gggaagagcg    12000
ggcctgtgga ggacttcgtg tccctggcga tggtgggcgg ccacctggag ttccgctatg    12060
agttggggtc agggctggcc gttctgcgga gcgccgagcc gctggccctg gccgctggc    12120
accgtgtgtc tgcagagcgt ctcaacaagg acggcagcct gcgggtgaat ggtggacgcc    12180
ctgtgctgcg ctcctcgccc ggcaagagcc agggcctcaa cctgcacacc ctgctctacc    12240
tgggggtgt ggagccttcc gtgccactgt ccccggccac caacatgagc gctcacttcc    12300
gcggctgtgt gggcgaggtg tcagtgaatg gcaaacggct ggacctcacc tacagtttcc    12360
taggcagcca gggcatcggg caatgctatg atagctcccc atgtgagcgc cagccttgcc    12420
aacatggtgc cacgtgcatg cccgctggcg agtatgagtt ccagtgcctg tgtcgagatg    12480
gattcaaagg agacctgtgt gagcacgagg agaacccctg ccagctccgt gaaccctgtc    12540
tgcatggggg cacctgccag ggcacccgct gcctctgcct ccctggcttc tctggcccac    12600
gctgccaaca ggctctggac atggcatag cagagtccga ctggcatctt gaaggcagcg    12660
ggggcaatga tgcccctggg cagtacggag cctatttcca cgatgatggc ttcctcgcct    12720
tccctggcca tgtcttctcc aggagcctgc ccgaggtgcc cgagaccatc gagctggagg    12780
ttcggaccag cacagccagt ggcctcctgc tctggcaggg tgtggaggtg ggagaggccg    12840
gccaaggcaa ggacttcatc agcctcgggc ttcaagacgg gcaccttgtc ttcaggtacc    12900
agctgggtag tgggaggcc cgcctggtct ctgaggaccc catcaatgac ggcgagtggc    12960
accgggtgac agcactgcgg gagggccgca gaggttccat ccaagtcgac ggtgaggagc    13020
tggtcagcgg ccggtcccca ggtcccaacg tggcagtcaa cgccaagggc agcgtctaca    13080
```

-continued

```
tcggcggagc ccctgacgtg gccacgctga ccggggcag attctcctcg ggcatcacag   13140
gctgtgtcaa gaacctggtg ctgcactcgg cccgacccgg cgccccgccc ccacagcccc   13200
tggacctgca gcaccgcgcc caggccgggg ccaacacacg ccctgcccc tcgtaggcac    13260
ctgcctgccc cacacggact cccgggccac gccccagccc gacaatgtcg agtatattat   13320
tattaatatt attatgaatt tttgtaagaa accgaggcga tgccacgctt tgctgctacc   13380
gccctgggct ggactggagg tgggcatgcc accctcacac acacagctgg gcaaagccac   13440
aaggctggcc agcaaggcag gttggatggg agtgggcacc tcagaaagtc accaggactt   13500
ggggtcagga acagtggctg ggtgggccca gaactgcccc cactgtcccc ctacccaccg   13560
atggagcccc cagatagagc tgggtggcct gtttctgcag cccttgggca gttctcactc   13620
ctaggagagc caacctcggc ttgtgggctg gtgccccaca gctacctgag acgggcatcg   13680
caggagtctc tgccacccac tcaggattgg gaattgtctt tagtgccggc tgtggagcaa   13740
aaggcagctc acccctgggc aggcggtccc catccccacc agctcgtttt tcagcacccc   13800
cacccacctc cacccagccc ctggcacctc ctctggcaga ctcccctcc taccacgtcc    13860
tcctggcctg cattcccacc ccctcctgcc agcacacagc ctggggtccc tccctcaggg   13920
gctgtaaggg aaggcccacc ccaactctta ccaggagctg ctacaggcag agcccagcac   13980
tgatagggcc ccgccaccg ggccccgccc accccaggcc acatcccac ccatctggaa     14040
gtgaaggccc agggactcct ccaacagaca acggacggac ggatgccgct ggtgctcagg   14100
aagagctagt gccttaggtg ggggaaggca ggactcacga ctgagagaga gaggaggggg   14160
atatgaccac cctgccccat ctgcaggagc ctgaagatcc agctcaagtg ccatcctgcc   14220
agtggccccc agactgtggg gttgggacgc ctggcctctg tgtcctagaa gggaccctcc   14280
tgtggtcttt gtcttgattt ttcttaataa acggtgctat ccccgcc                 14327
```

WOUND AND CUTANEOUS INJURY HEALING WITH A NUCLEIC ACID ENCODING PERLECAN

FIELD OF DISCLOSURE

The present disclosure relates to biomolecules involved in wound healing and angiogenesis.

BACKGROUND

Perlecan, originally named heparan sulfate proteoglycan, is now known to be an important component of all basement membranes (along with collagen type IV and laminin) and is thought to play a role in wound healing and angiogenesis. Perlecan consists of three heparan sulfate side chains linked to a large core protein of approximately 450 kDa (32, 36). This sequence has a single open reading frame of at least 3,707 amino acids that encodes for a protein of 396–466 kDa. Sequence analysis of the deduced sequences show the protein consists of five different domains, most of which contain internal repeats. Domain I contains a start methionine followed by a typical signal transfer sequence and a unique segment of 172 amino acids that contains the three probable sites of heparan sulfate attachment (of the amino acid sequence SGD). Domain II contains four strictly conserved cysteine-rich and acidic amino acid repeats that are very similar to those found in the LDL receptor and proteins such as megalin/GP330. Domain III consists of cysteine-rich and globular regions, both of which show similarity to those in the short arm of the laminin A chain. Domain IV contains 14 repeats of the immunoglobulin superfamily that are most highly similar to the immunoglobulin-like repeats in the neural cell adhesion molecule, and it appears domain IV has the capacity for differential splicing. Recombinant domain IV of perlecan binds to nidogens, laminin-nidogen complex, fibronectin, fibulin-2 and heparin (24). Domain V is the COOH-terminal domain and contains three repeats with similarity to the laminin A chain G domain. The repeats are separated by epidermal growth factor-like regions not found in the laminin A chain. Perlecan domain V is considered important in the supramolecular assembly of, and cell connections to, basement membranes (5).

The primary structural data agree with the appearance of the molecule in the electron microscope as a series of globules separated by rods, or "beads on a string." Therefore, the name perlecan was adopted for this molecule (36). In summary, the variety of domains in perlecan suggests multiple interactions with other molecules, and each domain of native perlecan has the potential for separate functional activities related to wound healing and/or angiogenesis.

Expression of Perlecan

Native perlecan has been purified from the mouse Englebroth Holm Swarm (EHS) tumor (22), porcine kidneys (16), bovine kidneys (21), from the conditioned medium of bovine aortic endothelial cells (39), and from the extracellular matrix of cultured human fetal lung fibroblasts (2). Other sources of perlecan may also be available and the above list is not meant to be inclusive. The individual domains of perlecan have also been individually expressed in native configuration from bacterial hosts (33) and eukaryotic hosts (8, 10, 20). The obvious domain structure and limited susceptibility to proteolysis (11) contribute to the ability to produce each of the perlecan domains individually. For example, domain 1 has been cloned and expressed alone (10, 19), and with portions of domain II (20). It is known that sequences in the protein core affect the amount and type of glycosaminoglycan (such as heparan sulfate) which is attached when perlecan is produced in a eukaryotic host. However, the biological significance of the different glycosylation patterns remains unknown.

In situ hybridization studies and immunoenzymatic studies show a close association of perlecan with a variety of cells involved in the assembly of basement membranes, in addition to being localized within the stromal elements of various connective tissues. Perlecan has been demonstrated in periodontal ligament fibroblasts (29). Perlecan has also been detected in the basement membranes of human tissues including pituitary gland, skin, breast, thymus, prostate, colon, liver, pancreas, spleen, heart, and lung. All vascular basement membranes reported to be tested contained perlecan. In addition, sinusoidal vessels of liver, spleen, lymph nodes, and pituitary gland expressed high levels of perlecan in the subendothelial region. In situ hybridization, using as probe human cDNA-encoding Domain III, localized perlecan mRNA to specific cell types within the tissues and demonstrated that in skin, perlecan appears to be synthesized exclusively by connective tissue cells in the dermal layer (32, 33). Perlecan is also highly expressed in human bone marrow (28) and in synovium (13). An immunohistochemical study confirmed the location of perlecan on the apical cell surface of endothelial cells, and additionally as a dense fibrillar network surrounding the cells. In this context, the binding of thromobospondin 1 to the apical surface of endothelial cells, which is critical in angiogenesis (44), was found to be dependent upon the $NH_2$-terminal heparan sulfate chains of perlecan (45). These patterns of perlecan expression clearly implicate a role in wound healing regulation and/or angiogenesis.

Cell and Growth Factor Binding

Perlecan is adhesive for fibroblasts and endothelial cells (28). Expression of perlecan in the mouse was coordinated with development of attachment competence by mouse embryos in vitro and in utero (7). Purified perlecan and laminin were found to promote attachment of immortalized rat chondrocytes in vitro (43). Perlecan is thought to modulate binding between the basement membrane structure and various cells, including smooth muscle cells and aortic endothelial cells, through a non-RGD cell binding region in one of the perlecan domains (possibly domain III in the mouse; amino acid sequence LPASFRGDKVTSY (SEQ ID NO: 1), as well as by GRGDSP (SEQ ID NO: 2), but not GRGESP (SEQ ID NO: 3)) and integrins $\beta$-1 and $\alpha$-5, $\beta$-3 (23). Alternatively, other investigators have found that the attachment of Rugli cells (a rat glioma derived cell line), mesenchymal, and epithelial derived tumor cell lines to mouse perlecan did not involve the protein core and was totally dependent on the presence of the heparan sulfate, although binding through the $\beta$-1 integrin of the cells was involved (4). Cell adhesion to perlecan was low compared to perlecan core alone (23). Human endothelial cell-derived perlecan was shown to bind endothelial cells in vitro with contributions from the heparan sulfate and from the protein core (46). The attachment of cells to the protein core of human perlecan further supports the implication of alternative cell binding pathways as the human homologue does not have the RGD sequence in domain III. Significant evidence for a role in cell binding further implicates perlecan in wound healing processes.

Proteoglycans such as perlecan, once thought to primarily serve as structural components of extracellular matrix, are now being focused on for their role in tissue and cell regulation, particularly angiogenesis and wound healing. Many growth factors, notably the fibroblast growth factor family (FGF) which now numbers 19 members, bind to heparin and heparan sulfate proteoglycans, and this binding has been shown to have a significant impact on the availability and activity of these growth factors. Importantly, perlecan has been shown to specifically bind to FGF-2 (also known as bFGF), which is critical in vascular development and wound healing (37). Perlecan was found to induce high affinity binding of FGF-2 both to cells deficient in heparan sulfate and to soluble FGF receptors. Further, in a rabbit ear model for in vivo angiogenesis, perlecan was a potent inducer of FGF-2-mediated neovascularization (2). It has been shown that FGF-2 binds to the heparin sulfate on domain I of perlecan (2) and that FGF-2 is released by biologically relevant enzymes such as plasmin, collagenase, and heparinases, which may have a role in the regulation of the growth factor activity (47). Mitogenic keratinocyte growth factor (FGF-7) was recently shown to bind to domains III and V of the perlecan protein core (31). Binding of FGF-2 to the heparan sulfate chain of perlecan is thought to involve three-way coordinated binding between FGF, heparan sulfate, and the FGF receptor, and to involve specific sites of sulfation (unpublished data). The FGF receptor is probably the FGF-binding protein that was recently reported to bind perlecan specifically in domain III (30).

Perlecan is also able to bind the growth factor granulocyte/macrophage-colony stimulating factor and present it to hematopoietic progenitor cells in a semi-solid colony assay (28). Bound growth factors can be released by enzymes, which are present during wound healing, such as the matrix metalloproteinases (47). Ligand binding itself can lead to internalization through a perlecan-mediated process, as has been shown for ligands such as lipoproteins (15). Binding of growth factors is clearly an important role of perlecan in wound healing and angiogenesis.

Breached basement membranes in vascular, corneal, and dermal tissues must respond quickly to the injury with repair. Such a rapid response suggests storage of needed biomolecules to effect repairs and remodeling. Cells involved in the wound healing and angiogenic process may have a ready and ample storage of FGF and other growth factors bound to perlecan in the basement membrane adjoining the wound. It has been demonstrated that enzymes which are turned on in the remodeling wound and angiogenesis, such as the matrix metalloproteinases (MMPs), stromelysin, rat collagenase, plasmin, urokinase, heparitinase I, and heparin, may modulate the bioavailability of the growth factors by degrading the protein core and removing the glycosaminoglycans (47). The MMPs are required in correct wound healing and in angiogenesis, and have been shown to bind to cells. The extracellular binding of MMPs could position the enzyme for directed proteolytic attack, for activation of other MMPs, and for regulation of other cell surface proteins. It has recently been demonstrated that heparin binds (5–10 nM) MMP-7, MMP-2, MMP-9, and MMP-13. This suggests that the MMPs may be positioned on the cell surface or retained in the ECM by perlecan heparan sulfate chains (48).

Growth and Wound Healing The effectiveness of perlecan as an exogenously added promoter of growth and neovascularization was demonstrated with anti-sense perlecan knockouts in colon carcinoma cells (40). Growth of colon carcinoma cells was markedly attenuated upon obliteration of perlecan gene expression and these effects correlated with reduced responsiveness to, and affinity for, FGF-7. Exogenous perlecan effectively reconstituted the activity of FGF-7 in the perlecan-deficient cells. Moreover, soluble FGF-7 specifically bound immobilized perlecan in a heparan sulfate-independent manner. In both tumor xenografts induced by human colon carcinoma cells and tumor allografts induced by highly invasive mouse melanoma cells, perlecan suppression caused substantial inhibition of tumor growth and neovascularization. Thus, perlecan is a potent inducer of cell growth and angiogenesis in vivo and therapeutic interventions targeting this key modulator of tumor progression may improve wound healing.

In cells that were expressing antisense perlecan, responses to increasing concentrations of FGF-2 were dramatically reduced in comparison to wild-type or vector-transfected cells as measured by thymidine incorporation and rate of proliferation (3). Furthermore, receptor binding and affinity labeling of cells expressing antisense perlecan indicated that eliminating perlecan expression (by expressing antisense perlecan) results in reduced high-affinity FGF-2 binding. Both the binding and mitogenic response of cells expressing antisense perlecan to FGF-2 could be rescued by exogenous perlecan (3).

Poor wound healing in diabetics and in diabetes-related periodontitis may be related to perlecan expression. High levels of glucose can decrease perlecan expression in some cells, probably through transcriptional and post-transcriptional mechanism (27). Further, it has recently been demonstrated that FGF-2 bound to perlecan is protected from inactivation by non-enzymatic glycation, which occurs during the course of diabetes (35). The relationship between poor expression and protection from inactivation in diabetes has not been investigated.

Evidence indicates that in cases of poor surgical wound closure and healing by frank secondary intention, as results in many barrier membrane surgeries during oral and periodontal surgeries, for example, the presence of perlecan in the subepithelial matrix is associated with healing of the wound up to 14 days post surgery, at which time the healed wound can appear normal in terms of perlecan core protein. Subsequently, sulfation levels of the heparan sulfate chains increase over the ensuing year of healing (1). Another investigation, however, reported that perlecan is not detectable under epithelial cells migrating over connective tissue and only appears when the wound is covered and a new basement membrane is deposited (38). In wounds that are remodeling over a period of weeks, perlecan levels in the subepithelial connective tissues appear to remain relatively high (42). The functional significance of various perlecan expression patterns during healing is not yet known, but it is clear the biomolecule has an important and fundamental role in the healing process.

In summary, a complex interplay exists between 1) extracellular matrix proteins, including perlecan, 2) the cells considered key in establishing dermal integrity such as fibroblasts, endothelial cells, epithelial cells, and 3) growth factors such as the FGF's. It is clear, however, that perlecan has the potential to affect several aspects of wound healing and, to that end, is an excellent candidate for application or induction in various forms, with or without the addition of various growth factors to modulate wound healing.

SUMMARY

The present disclosure describes the use of perlecan as an adjunct for the improvement of wound healing and/or angiogenesis. The disclosure describes the application of perlecan at an effective concentration in a pharmaceutically acceptable carrier, such as a paste, for use in a variety of processes. For example, perlecan may be used during periodontal procedures, such as flap surgery, or may be applied to sites of cutaneous injury such as burns and cuts, or may be applied to sites of surgical procedures, such as incisions, implants or grafts. Perlecan may be applied directly in a pharmaceutically acceptable carrier, or may be applied to a wound bandage or dressing, or may be absorbed to surgical implants, grafting materials or surgical barrier membranes. Perlecan may also be applied by delivery of nucleic acid encoding for perlecan. Perlecan nucleic acid may be delivered via viral vectors, cells expressing perlecan molecules, via naked nucleic acid (such as mRNA) or via liposome technology The present disclosure also encompasses the application of perlecan in conjunction with growth factors, such as FGF-2 or FGF-7, or other heparan sulfate binding growth factors. Evidence suggests that perlecan or its derivatives has the potential to effect the interplay between cells of the dermis and epidermis, the extracellular matrix, and various growth factors, each of which has a role in wound healing and or angiogenesis. Therefore, perlecan is an excellent candidate for application or delivery in various forms, possibly in conjunction with various growth factors, to modulate wound healing and/or angiogenesis.

DETAILED DESCRIPTION

In the present disclosure, the use of perlecan as an adjunct to wound healing and angiogenesis is described. As used in this specification and claims, the term "perlecan" refers to the polypeptide listed in SwissProt Protein Data Base named Heparan Sulfate Proteoglycan (accession number CAC18534.1) (SEQ ID NO: 4) or the nucleic acid coding sequence named Human Heparan Sulfate Proteoglycan (HSPG2) mRNA (GenBank accession number M85289.1) (SEQ ID NO: 5). In addition to the perlecan nucleic acid sequences disclosed in SEQ ID NO: 5, the present disclosure also is directed to nucleic acid sequences encoding functional derivatives of the perlecan nucleic acid. As used herein, a "functional derivative"-includes the "fragments," "degenerate variants," "mutants," "analogs," "variants" and "chemical derivatives". The term "fragment" is meant to refer to any nucleic acid subset of the perlecan nucleic acid comprising at least 9 contiguous nucleic acid residues. The term "variant" is meant to refer to a molecule substantially similar in structure to either the entire cpk gene, or to a fragment thereof. The term "chemical derivative" describes a nucleic acid or protein that contains additional chemical moieties which are not normally a part of the base molecule. Such moieties may alter the solubility, binding characteristics (to molecules such as growth factors) half-life, absorption, etc. of the base molecule. Alternatively the moieties may attenuate undesirable side effects of the base molecule or decrease the toxicity of the base molecule. Examples of such moieties are described in a variety of texts, such as *Remington The Science and Practice of Pharmacy*, 20$^{th}$ edition.

It is known that there is a substantial amount of redundancy in the codons which code for specific amino acids. Therefore, this disclosure is directed to those nucleic acid sequences which contain alternative codons which code for the eventual translation of the identical amino acid in SEQ. ID NO. 4. For purposes of this specification, a nucleic acid sequence coding for one or more alternative codons will be defined as a "degenerate variation." Also included within the scope of this disclosure are mutations either in the perlecan nucleic acid sequence which do not substantially alter the ultimate physical properties of the polypeptide encoded by the perlecan nucleic acid, or functional derivatives thereof (referred to as an "analog"). For example, an analog may comprise a conservative amino acid changes, such as, but not limited to, substitution of valine for leucine or asparagine for glutamine. Other examples of conservative amino acid changes may be found in Biochemistry, 2cd Edition Geoffrey Zubay (Macmilliam Publishing Company, New York, New York, Table 1—1, p33) and include substitutions of an amino acids with other amino acid listed within the same grouping. It is known that DNA sequences coding for a polypeptide may be altered so as to code for a peptide having properties that are different than those of the naturally-occurring peptide (referred to as "mutants"). Mutant nucleic acid sequences may be isolated from nature (as is the case for SEQ ID NO. 6). Methods of producing mutant nucleic acid sequences include, but are not limited to site directed mutagenesis. Examples of altered properties include, but are not limited to changes in the affinity of an enzyme for a substrate or a receptor for a ligand (such as but not limited to growth factors) and altered sulfation patterns. A molecule is "substantially similar" to the cpk nucleic acid if both molecules have substantially similar structures, or if both molecules possess similar biological activity.

The disclosure also directed to polypeptides encoded by perlecan nucleic acid, or functional derivatives thereof. Therefore, the disclosure covers polypeptides coded for by fragments of the perlecan nucleic acid. In addition, the disclosure covers polypeptides coded for by analogs, degenerate variants and mutants of the perlecan nucleic acid.

A molecule is "substantially similar" to perlecan in terms of structure if both molecules have more than 50% similarity or 70% identity between their respective nucleotide or amino acid sequences. Forms of perlecan that varied in glycosaminoglycan profiles and sulfation patterns, including those forms of perlecan totally without glycosaminoglycan or sulfated constituents, would be considered molecules substantially similar to perlecan. As used in this disclosure, the term "percent homology" of two amino acid sequences or of two nucleic acid sequences is determined using the algorithm of Karlin and Altschul (Proc. Natl. Acad. Sci. USA 87: 2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215: 403–410, 1990). Blast nucleotide searches are performed with the NBLAST program, score=100, wordlength=12, to obtain nucleotide sequences homologous to a nucleic acid molecule of the invention. Blast protein searches are performed with the XBLAST program, score=50, wordlength=3 to obtain amino acid sequences homologous to a referenced polypeptide. To obtain gapped alignments for comparison purposes, Gapped BLAST is utilized as described in Altschul et al. (Nucleic Acids Res. 25:3389–3402, 1997). When utilizing BLAST and Gapped BLAST programs, the default parameters of the respective programs (XBLAST and NBLAST) are used. See http://www.ncbi.nlm.nih.gov.

Perlecan may be derived from purification from either natural or recombinant sources, standard cloning procedures, from proteolysis of cloned or native molecules, or by induction within host cells, or by delivery from cells expressing perlecan nucleic acid sequences. For example, a derivative of perlecan would include a recombinant perlecan protein expressed from a host cell where the fragment comprised both domains I and III of the native perlecan molecule, and where the nucleic acid coding for the recombinant perlecan molecule was mutated to alter the sulfation pattern when compared to native perlecan. In addition, perlecan may be used either alone or in the presence of a modulating compound (defined as a protein, nucleic acid or organic compound that modulates the structure and/or function and/or activity of perlecan). Examples of modulating compounds are growth factors, especially those growth factors of the fibroblast growth factor family, such as FGF-2 and FGF-7, and other growth factors that interact with the heparan sulfate chains.

As used in this disclosure, an isolated nucleic acid is a nucleic acid the structure of which is not identical to that of any naturally occurring nucleic acid, or to that of any fragment of a naturally occurring genomic nucleic acid spanning more than three separate genes. The term therefore covers, by way of example only, 1) a DNA which has the sequence of part of a naturally occurring genomic DNA molecule, but is not flanked by both of the sequences that flank that part of the molecule in the genome of the organism in which it naturally occurs; 2) a nucleic acid incorporated into a vector or into the genomic DNA of a prokaryote or eukaryote in a manner such that the resulting molecule is not identical to any naturally occurring genomic DNA; 3) a separate molecule such as a cDNA, a genomic fragment, a fragment produced by PCR, or a restriction fragment; and 4) a recombinant nucleotide sequence that is part of a hybrid gene (i.e., a gene encoding a fusion protein). Specifically excluded from this definition are nucleic acids present in mixtures of DNA molecules, transfected cells and cell clones, as these occur in a DNA library such as a cDNA or genomic library.

Perlecan may be recombinantly expressed either alone or in combination with a modulating compound by molecular cloning into an expression vector containing a suitable promoter and other appropriate transcription regulatory elements, and transferred into prokaryotic or eukaryotic host cells to produce recombinant molecules. Techniques for such manipulations are within the ordinary skill of one in the art, and representative techniques can be found described in Sambrook, J., et al., *Molecular Cloning Second Edition*, 1990, Cold Spring Harbor Press. Expression vectors are defined herein as the nucleic acid sequences that are required for the transcription of cloned copies of genes and the translation of their mRNAs in an appropriate host. Such vectors can be used to express eukaryotic genes in a variety of hosts such as bacteria, blue green algae, plant cells, insect cells, fungal cells and animal cells.

An appropriately constructed expression vector should contain, at the minimum: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. Expression vectors may include, but are not limited to, cloning vectors, modified cloning vectors, specifically designed plasmids or viruses.

A variety of expression vectors may be used for the expression of perlecan. These include, but are not limited to commercially available mammalian expression vectors such as pcDNA3 (Invitrogen), pMC1neo (Stratagene), pXT1 (Stratagene), pSG5 (Stratagene), EBO-pSV2-neo (ATCC 37593) pBPV-1 (8-2) (ATCC 37110), pdBPV-MMTneo (342-12) (ATCC 37224), pRSVgpt (ATCC 37199), pRSV-neo (ATCC 37198), pSV2-dhfr (ATCC 37146), pUCTag (ATCC 37460), and 1ZD35 (ATCC 37565).

Commercially available bacterial expression vectors that may be suitable for recombinant expression of perlecan include, but are not limited to, pET11a (Novagen), lambda gt11 (Invitrogen), pcDNAII (Invitrogen), pKK223-3 (Pharmacia). Commercially available insect cell expression vectors that may be suitable for recombinant expression of perlecan include, but are not limited to, pBlue Bac III (Invitrogen). The expression vectors may also be produced according to specific needs. The choice of the appropriate expression vector is within the ordinary skill of one in the art. The expression vector may contain nucleic acid coding only for the perlecan, or may encode for the perlecan, either alone or in combination with a modulating compound.

Recombinant host cells may be prokaryotic or eukaryotic, including but not limited to bacteria such as *E. Coli*, fungal cells such as yeast, and mammalian cells, including, but not limited to, cell lines of human, bovine, porcine, monkey and rodent origin, and insect cells including, but not limited to, *Drosophila* and silkworm derived cell lines. A variety of cell lines derived from mammalian species which may be suitable for use as host cells are commercially available and include, but are not limited to, L cells L-M (TK.sup.-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171). The choice of host cells is within the ordinary skill of one in the art.

The expression vectors may be introduced into host cells via any one of a number of techniques including but not limited to transformation, transfection, lipofection, protoplast fusion, and electroporation. The expression vector-containing cells are clonally propagated and individually analyzed to determine whether they produce the compound of interest. Identification of cells expressing the perlecan product, can be accomplished by a variety of means, including but not limited to, immunological reactivity, or the presence of host cell-associated perlecan activity.

Expression of perlecan, either alone or in combination with a modulating compound, may also be performed using in vitro produced synthetic mRNA or isolated native mRNA. Synthetic mRNA or mRNA isolated from perlecan producing cells can be efficiently translated in various cell-free systems, including but not limited to wheat germ extracts and reticulocyte extracts, as well as efficiently translated in cell based systems, including but not limited to microinjection into frog oocytes.

Following expression of perlecan in a recombinant host cell, which host cell may also be expressing a modulating compound, purified perlecan, or purified perlecan in association with a modulating compound may be obtained. Purification methods for isolating expressed protein are well known in the art and within the ordinary skill in the art. Techniques include salt fractionation, ion exchange chromatography, size exclusion chromatography, hydroxylapatite adsorption chromatography, hydrophobic interaction chromatography, immunoaffinity chromatography and affinity chromatography.

Mono-specific antibodies to human perlecan can be purified from mammalian antisera containing antibodies reactive against perlecan, or are prepared as monoclonal antibodies reactive with perlecan. Mono-specific antibody is defined as a single antibody species, or multiple antibody species with binding characteristics for perlecan, and includes polyclonal antibodies. Homogenous binding as used herein refers to the ability of the antibody species to bind to a specific antigen or epitope. Specific antibodies are raised by immunizing animals such as mice, rats, guinea pigs, rabbits, goats, horses and the like, with rabbits being preferred, with an appropriate concentration of perlecan, either with or without an immune adjuvant.

Preimmune serum is collected prior to the first immunization to establish baseline immunoreactivity. Each animal receives between about 0.1 mg and about 1000 mg of perlecan, either with or without an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of perlecan, and preferably Freund's complete adjuvant, at multiple sites either subcutaneously (SC), intraperitoneally (IP), or both. Each animal is bled at regular intervals, preferably weekly, to determine antibody titer. The animals may or may not receive booster injections following the initial immunization. Those animals receiving booster injections are generally given an equal amount of the initial antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20 degree C.

Monoclonal antibodies (mAb) reactive with perlecan are prepared by immunizing inbred mice, preferably Balb/c, with the appropriate antigen. The mice are immunized by the IP or SC route with about 0.1 mg to about 10 mg, preferably about 1 mg, of antigen in about 0.5 ml buffer or saline incorporated in an equal volume of an acceptable adjuvant, as discussed above. Freund's complete adjuvant is preferred. The mice receive an initial immunization on day 0 and are rested for about 2 to about 30 weeks. Immunized mice are given one or more booster immunizations of about 0.1 to about 10 mg of antigen in a buffer solution such as phosphate buffered saline by the subcutaneous or intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 molecular weight, at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay using perlecan as the antigen. The culture fluids are also tested in the Ouchterlony precipitation assay and ELISA to determine the isotype of the mAb. Hybridoma cells from antibody positive wells are cloned by techniques well know in the art.

It is readily apparent to those skilled in the art that the above described methods for producing monospecific antibodies may be utilized to produce antibodies specific for the isolated perlecan, either alone or in combination with a modulating compound.

The antibodies produced above may be used as affinity columns by adding the antibodies to Affigel-10 (Biorad, Hercules, Calif.), according to the manufacturer's directions. After coupling of the antibodies to the column, the column is washed with water followed by 0.23M glycine HCl (pH 2.6) to remove any non-conjugated antibody or extraneous protein. The column is then equilibrated in phosphate buffered saline (pH 7.3) with appropriate detergent, and the cell culture supernatants or cell extracts containing perlecan, ether alone or in combination with a modulating compound, made using appropriate membrane solubilizing detergents are slowly passed through the column. The column is then washed with phosphate buffered saline/detergent until the optical density ($A_{280}$) falls to background, then the protein is eluted with 0.23M glycine-HCl (pH 2.6)/detergent. The purified protein is then dialyzed against phosphate buffered saline/detergent.

The present invention is also directed to methods for screening for compounds which modulate the expression of nucleic acid encoding perlecan, and/or the function of perlecan protein, in vivo and in vitro, either alone or in combination with a modulating compound. Compounds which modulate these activities may be DNA, RNA, peptides, proteins, or non-proteinaceous organic molecules. Compounds may modulate by increasing or attenuating the expression of DNA or RNA encoding perlecan or the function of the perlecan protein, either alone or in combination with a modulating compound. Compounds that modulate the expression of nucleic acid encoding perlecan, and/or the function of perlecan protein may be detected by a variety of assays. The assay may be a simple "yes/no" assay to determine whether there is a change in expression or function. The assay may be made quantitative by comparing the expression or function of a test sample with the levels of expression or function in a standard sample. The expression of perlecan protein, either alone or in combination with a modulating compound, is performed as described above. Such an assay is directed to direct inhibitors of perlecan nucleic acid expression or perlecan activity, as well as indirect inhibitors of this activity.

Kits containing perlecan nucleic acids or antibodies to perlecan may be prepared. Such kits can be used to detect nucleic acids which hybridize to the perlecan nucleic acids, or to detect the presence of perlecan protein or proteoglycan in a sample. In addition, such kits would contain the accessory reagents required to complete the assay contemplated by the kit.

Nucleotide sequences complementary to the nucleotide sequences coding for perlecan can be synthesized for antisense therapy. These antisense molecules may be DNA, stable derivatives of DNA such as phosphorothioates or methylphosphonates, RNA, stable derivatives of RNA such as 2'-O-alkylRNA, or other antisense oligonucleotide mimetics. These antisense molecules may be introduced into cells by microinjection, liposome encapsulation or by expression from vectors harboring the antisense sequence. Antisense therapy may be particularly useful for the treatment of diseases where it is beneficial to reduce perlecan activity.

Gene therapy may be used to introduce perlecan either alone or in combination with a modulating compound, into the cells. The nucleic acid coding for the appropriate protein can be ligated into viral vectors which mediate transfer of the DNA by infection of recipient host cells. Suitable viral vectors include retrovirus, adenovirus, adeno-associated virus, herpes virus, vaccinia virus, polio virus and the like. Alternatively, DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo, as well as in vivo gene therapy. Gene therapy may be particularly useful for the treatment of diseases where it is beneficial to elevate perlecan activity.

Pharmaceutically useful compositions comprising nucleic acids and their complements, and proteins corresponding to perlecan, either alone or in combination with modulating compounds, may be formulated according to known methods such as by the admixture of a pharmaceutically acceptable carrier. Examples of such carriers and methods of formulation may be found in *Remington's Pharmaceutical Sciences*. To form a pharmaceutically acceptable composition suitable for effective administration, such compositions will contain an effective amount of the protein, nucleic acid, or modulator compound.

Therapeutic or diagnostic compositions of the invention are administered to an individual in amounts sufficient to treat and/or diagnose disorders related to perlecan (defined as the "effective amount"). The effective amount may vary according to a variety of factors such as the individual's condition, weight, sex and age. Other factors include the mode or site of administration. The pharmaceutical compositions may be provided to the individual by a variety of routes such as subcutaneous, topical, oral, intraosseous, and intramuscular. Compounds identified according to the methods disclosed herein may be used alone at appropriate dosages defined by routine testing in order to obtain optimal activity, while minimizing any potential toxicity. In addition, co-administration or sequential administration of other agents may be desirable.

The therapeutic or diagnostic derivatives of perlecan discussed herein may be used with or without chemical derivatives. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

The compositions containing compounds identified according to this invention as the active ingredient for use in the modulation of wound healing and/or angiogenesis can be administered in a wide variety of therapeutic dosage forms in conventional vehicles for administration. For example, the compounds can be administered in such forms as tablets, capsules (each including timed release and sustained release formulations), pills, powders, granules, elixirs, tinctures, solutions, suspensions, syrups, pastes and emulsions, or by injection internally.

In the present disclosure, the compounds herein described in detail can form the active ingredient, and are typically administered in admixture with suitable pharmaceutical diluents, excipients or carriers, which are collectively referred to herein as "carrier" materials, suitably selected with respect to the intended form of administration, that is, oral tablets, capsules, elixirs, syrups and the like, and consistent with conventional pharmaceutical practices. For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like.

For oral forms, the active biologic component can be combined in suitably flavored suspending or dispersing agents such as the synthetic and natural gums, for example, tragacanth, acacia, methylcellulose and the like. Other dispersing agents that may be employed include glycerin and the like. For internal injection, sterile suspensions and solutions are desired. Isotonic preparations that generally contain suitable preservatives are employed when internal injection is desired.

Topical preparations containing the active drug component can be admixed with a variety of carrier materials well known in the art, such as, e.g., alcohols, aloe vera gel, allantoin, glycerine, vitamin A and E olis, mineral oil, PPG2 myristyl propionate, and the like, to form, e.g., alcoholic solutions, topical cleansers, cleansing creams, skin gels, skin lotions, and shampoos in cream or gel formulations.

The compounds of the present disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present disclosure may also be delivered by the use of monoclonal antibodies as individual carriers to which the compound molecules are coupled. The compounds of the present disclosure may also be coupled with soluble polymers as targetable drug carriers. Such polymers can include, but are not limited to, polyvinylpyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

All references to articles, books, patents, websites and other publications in this disclosure are considered incorporated by reference. The following examples illustrate certain embodiments of the present disclosure without, however, limiting the same thereto.

PROPHETIC EXAMPLES

Use of Perlecan in Surgical Procedures including Periodontal Procedures

In one embodiment, perlecan would be purified from eukaryotic or bacterial cells via standard cell culture and protein purification methodology. Exemplary cell types, cell growth conditions and antibodies for affinity purification of perlecan from cultured eukaryotic cells have been described (2, 16, 21, 22, 39). Eukaryotic cells may be from primary culture or may be derived from cloned or immortalized cell lines (8, 10, 20). Antibody affinity chromatography may bemused to purify perlecan from either cell source (25, 34).

Various monoclonal antibodies that are specific for different epitopes of perlecan are available commercially and could be used in sequence to optimize purity. Purity would be established by molecular sieve chromatography and SDS-PAGE electrophoresis, or by other standard techniques (17). Purification of perlecan may be from cell culture media directly, or may involve fractionation of cells by standard methods and purification, such as isolation of and purification from intracellular inclusion bodies (26). Once released from inclusion bodies by standard techniques, affinity purification would follow as described above. Cloning of perlecan would involve standard PCR and ligation procedures into any number of suitable eukaryotic or bacterial expression vectors (6). Importantly, when perlecan is expressed in bacteria, it may be necessary to alter the nucleic acid sequence of perlecan to meet the requirements of the transcriptional and translation system of the bacterial host. These forms of perlecan, and the nucleic acid sequences coding for them, are included in the definition of perlecan derivative.

As discussed above, perlecan would include those with different sulfation patterns and differing amounts of glycosaminoglycan chains. The presence or absence of particular modifications may differ between eukaryotic and bacterial cells, and within different cells types within each class. In addition, perlecan may be administered with or without various growth factors. As discussed above, perlecan has been shown to bind certain growth factors and may play a role in regulating the activity of these growth factors. Therefore, it may be advantageous to administer perlecan with growth factors in certain situations. It is preferred that the perlecan is mixed with the growth factor prior to being incorporated into a pharmaceutically acceptable formulation. The molar ratio of perlecan to growth factor can range from 0.1 to 1 to 20 to 1, but a preferred ration is 1 to 1. Growth factors that may be used with perlecan include, but are not limited to, members of the fibroblast growth factor family, such as FGF-2 and FGF-7, and GM-CSF. Other growth factors determined to be active in either wound healing, tissue remodeling or angiogenesis may also be used with perlecan.

Perlecan may be incorporated into various pharmaceutically acceptable formulations for use as discussed above. In one embodiment perlecan may be mixed with a carrier paste. Various carrier pastes for dermal or surgical application are available and many are inert formulations based on cellulose. Perlecan is included in the paste at an effective concentration as discussed above. In one embodiment, the range of perlecan concentrations within the carrier paste is 1 pM to 1 µM. The perlecan (preferably in a pharmaceutically acceptable formulation, such as the paste described above) may be used during a variety of purposes. For example, during periodontal procedures, perlecan may be applied at the time of surgical closure between and below flaps. Approximately 1 ml of paste containing perlecan would be applied for every 6 cm$^2$ of wound surface, and would be applied liberally.

A variety of systems have been developed to accomplish expression of exogenous proteins via the delivery of nucleic acid sequences coding for the given protein into target cells. In one embodiment, perlecan would be delivered as an adjunct to wound healing or surgical healing by placing into the wound or surgical site cells which have been induced to express perlecan. These cells would have preferably been derived from the recipient, but may be of an allograft or xenograft nature, being derived from other human donors, or from animals. Cells may include stem cells, endothelial cells, epithelial cells, fibroblasts, monocytes or macrophages. The target cells will be collected from the blood or tissues of the donor by standard methods and nucleic acid coding for perlecan will be introduced into the cell. Methods of introducing the perlecan encoding nucleic acid into cells are well known in the art as described above. One such method involves infecting the target cells with a viral-based expression vector, such as adenovirus. Adenovirus containing perlecan encoding nucleic acid and target cells are mixed for 30 minutes in serum-free cell culture media. After this infection period, the cells will be collected by centrifugation and applied to the wound or surgical site at a density of between $10^3$–$10^6$ cells per cm$^2$.

In another embodiment, a nucleic acid fragment coding for perlecan would be delivered to the desired site in a viral-based expression vector. There are many choices for viral-based expression vectors which are well known in the art. However, a preferred viral vector is the adenovirus. There are several good reasons for utilizing recombinant adenovirus vectors for the delivery of nucleic acid encoding perlecan. First, stocks of adenovirus containing high titers of virus (greater than $10^{11}$ pfu per ml) can be prepared, which makes it possible to transduce cells in situ at high multiplicity of infection for high localized protein production. Also, the adenovirus is capable of inducing high levels of transgene expression, at least as an initial burst. Third, the vector can be engineered to incorporate a high degree of versatility. Finally, the adenovirus vector is safe based on its long-term use as a vaccine. Recombinant adenovirus vectors have been utilized as vaccine carriers by intranasal, intratracheal, intraperitoneal, intravenous, subcutaneous, or intramuscular routes (9, 12, 18). In this embodiment, nucleic acid encoding perlecan, such as cDNA will be ligated into a replication-incompetent, E1/E3 defective human adenovirus serotype 5-derived vector under the transcriptional control of the human cytomegalovirus early promoter as described previously (41). For inducing perlecan expression from said cDNA expression system, $10^5$ to $10^9$ adenovirus particles will be delivered per cm$^2$ of wound surface area, or per cm$^3$ of a surgical grafting site.

The exogenous perlecan encoding nucleic acid may also be incorporated into the pharmaceutically acceptable carriers described above for the uses discussed above. For example, perlecan encoding nucleic acid may be incorporated into a paste formulation as discussed above and used in surgical and periodontal procedures, such as flap surgery, or applied to cutaneous injuries, such as burns or cuts. In addition, perlecan encoding nucleic acids may be applied to grafting materials, implant materials, surgical barrier membranes and dressings for the purposes described below. As an example, perlecan encoding nucleic acid may be adsorbed onto the surface of an implant before implant placement by painting, spraying, or soaking the implant material in a sterile solution of exogenous perlecan encoding nucleic acid for periods of time ranging from 1 second to 24 hours.

Use of Perlecan for Cutaneous Injury

In this embodiment, perlecan is expressed and purified as discussed above. As discussed in Example 1, perlecan may be used in a variety of forms and in a variety of pharmaceutically acceptable formulations. As another example of perlecan use, perlecan may be applied to the surface of a site of cutaneous injury, such as a burn, a non-healing ulcer, or a cut or similar injury. Approximately 1 ml of paste containing perlecan would be applied for every 6 cm$^2$ of wound surface and would be applied liberally. In addition, the perlecan-containing paste may be delivered in association with a bandage or other dressing applied to the site of injury.

Use of Perlecan In Conjunction With Surgical Implants and Similar Materials

In this embodiment, perlecan is expressed and purified as discussed above. As discussed in Example 1, perlecan may be used in a variety of forms and in a variety of pharmaceutically acceptable formulations. As another example of perlecan use, perlecan may be applied to and absorbed on the surface of surgical implants, grafting material or barrier membranes.

Surgical implants include, but are not limited to, those made of titanium or titanium coated with hydroxy-apatite material. Bone grafting materials include, but are not limited to, hydroxyl apatite in various crystal sizes and forms, and autologous, autogenous, or xenograft donar bone, either cortical or cancellous, and freeze-dried with demineralization. Barrier membrane materials include, but are not limited to, poly vinyl difluoride (Gore-Tex), poly galactic acid, or collagen (BioMend). The surgical implants, grafting materials and barrier membrane would be pre-treated in a solution of perlecan, approximately 1 pM to 1 µM in concentration, preferably in a sterile buffer such as phosphate buffer, pH 7.4. The pre-treatment may be performed during surgery, or at any time prior to the surgery provided the coated surgical implant material is not subject to temperatures above 37° C. at any time. The pre-treatment procedure would involve immersion in the perlecan solution for at least 10 seconds, preferably 5 minutes. The treated membrane would then be surgically placed. As discussed above, various growth factors may also be incorporated into the perlecan solution for incorporation into and absorption onto the surgical implants, grafting materials and barrier membranes. Once prepared, the surgical implants, grafting materials and barrier membranes are used according to standard procedures.

REFERENCES

1. Andriesson M P, van den Born J, Latijnhouwers M A, Bergers M, van de Kerkhof P C, Schalkwijk J. Basal membrane heparan sulphate proteoglycan expression during wound healing in human skin. J. Pathol. 1997: 183: 251–252
2. Aviezer D, Hecht D, Safran M, Eisinger M, David G, Yayon A. Perlecan, basal lamina proteoglycan, promotes basic fibroblast growth factor-receptor binding, mitogenesis, and angiogenesis. Cell 1994: 79: 1005–1013
3. Aviezer D, Iozzo R V, Noonan D M, Yayon A. Suppression of autocrine and paracrine functions of basic fibroblast growth factor by stable expression of perlecan antisense cDNA. Mol. Cell Biol. 1997: 17: 1938–1946
4. Battaglia C, Aumailley M, Mann K, Mayer U, Timpl R. Structural basis of beta-I integrin-mediated cell adhesion to a large heparan sulfate proteoglycan from basement membranes. Eur. J. Cell Biol. 1993: 61: 92–99
5. Brown J C, Sasaki T, Gohring W, Yamada Y, Timpl R. The C-terminal domain V of perlecan promotes beta1 integrin-mediated cell adhesion, binds heparin, nidogen and fibulin-2 and can be modified by glycosaminoglycans. Eur. J. Biochem. 1997: 250: 39–46
6. Burke J F. PCR: essential techniques. Ed. Burke, J. F. New York: Wiley, 1996: 168.
7. Carson D D, Tang J P, Julian J. Heparan sulfate proteoglycan (perlecan) expression by mouse embryos during acquisition of attachment competence. Dev. Biol. 1993: 155: 97–106
8. Chakravarti S, Horchar T, Jefferson B, Laurie G W, Hassell J R. Recombinant domain III of perlecan promotes cell attachment through its RGDS sequence. J. Biol. Chem. 1995: 270: 404–409
9. Chen H H, Mack L M, Kelly R, Ontell M, Kochanek S, Clemens P R. Persistence in muscle of an adenoviral vector that lacks all viral genes. Proc. Natl. Acad. Sci. USA 1996: 94: 1645–1650
10. Costell M, Mann K, Yamada Y, Timpl R. Characterization of recombinant perlecan domain I and its substitution by glycosaminoglycans and oligosaccharides. Eur. J. Biochem. 1997: 243: 115–121
11. Costell M, Sasaki T, Mann K, Yamada Y, Timpl R. Structural characterization of recombinant domain II of the basement membrane proteoglycan perlecan. FEBS Letters 1996: 396: 127–131
12. Croyle M A, Anderson D J, Foessler B J, Amidon G L. Development of a highly efficient purification process for recombinant adenoviral vectors for oral gene delivery. Pharmaceutical Development Technology 1998: 3: 365–372
13. Dodge G R, Boesler E W, Jimenez S A. Expression of the basement membrane heparan sulfate proteoglycan (perlecan) in human synovium and in cultured human synovial cells. Lab. Investig. 1995: 73: 649–657
14. Dolan M, Horchar T, Rigatti B, Hassel J R. Identification of sites in domain I of perlecan that regulate heparan sulfate synthesis. J. Biol. Chem. 1997: 272: 4316–4322
15. Fuki I V, Iozzo R V, Williams K J. Perlecan heparan sulfate proteoglycan: a novel receptor that mediates a distinct pathway for ligand catabolism. J. Biol. Chem. 2000: 275: 25742–25750
16. Gauer S, Schulzelohoff E, Schleicher E, Sterzel R B. Glomerular basement membrane-derived perlecan inhibits mesangial cell adhesion to fibronectin. Eur. J. Cell Biol. 1996: 70: 233–242
17. Gersten DM. Gel electrophoresis: proteins essential techniques. Ed. Gersten, D. M. New York: Wiley Publishing, 1996: 192.
18. Gomez-Foix A M, Coats W S, Baque S, Alam T, Gerard R D, Newgard C B. Adenovirus-mediated transfer of the muscle glycogen phophorylase gene into hepatocytes confers altered regulation of glycogen metabolism. J. Biol. Chem. 1992: 267: 25129–25134
19. Graham L D, Whitelock J M, Underwood P A. Expression of human perlecan domain I as a recombinant heparan sulfate proteoglycan with 20-kDa glycosaminoglycan chains. Biochem. Biophys. Res. Comm. 1999: 256: 542–548
20. Groffen A J A, Buskens C A F, Tryggvason K, Veerkamp J H, Monnens L A H, Vandenheuvel L P W J. Expression and characterization of human perlecan domains I and II synthesized by baculovirus-infected insect cells. Eur. J. Biochem. 1996: 241: 827–834
21. Hagen S G, Michael A F, Butkowski R J. Immunochemical and biochemical evidence for distinct basement membrane heparan sulfate proteoglycans. J. Biol. Chem. 1993: 268: 7261–7269
22. Hassell J R, Robey P G, Barrach H-J, Wilczek J, Rennard S I, Martin G R. Isolation of a heparan sulfate-containing proteoglycan from basement membrane. Proc. Natl. Acad. Sci. USA 1980: 77: 4494–4498
23. Hayashi K, Madri J A, Yurchenco P D. Endothelial cells interact with the core protein of basement membrane perlecan through beta1 and beta3 integrins—an adhesion modulated by glycosaminoglycan. J. Cell Biol. 1992: 119: 945–959

24. Hopf M, Gohring W, Kohfeldt E, Yamada Y, Timpl R. Recombinant domain IV of perlecan binds to nidogens, laminin-nidogen complex, fibronectin, fibulin-2 and heparin. Eur. J. Biochem. 1999: 259: 917–925

25. Janson J-C, Ryden L. Protein purification: principles, high-resolution methods, and applications. Ed. Jansen, J.-C., and Ryden, L. New York: Wiley, 1998: 712.

26. Jones P. Vectors: expression systems: essential techniques. Ed. Jones, P. New York: Wiley, 1998:168.

27. Kasinath B S, Grellier P, Choudhury G G, Abboud S L. Regulation of basement membrane heparan sulfate proteoglycan, perlecan, gene expression in glomerular epithelial cells by high glucose medium. J. Cell Physiol. 1996: 167: 131–136

28. Klein G, Conzelmann S, Beck S, Timpl R, Muller C A. Perlecan in human bone marrow: a growth-factor-presenting, but anti-adhesive, extracellular matrix component for hematopoietic cells. Matrix Biol. 1995: 14: 457–465

29. Larjava H, Hakkinen L, Rahemtulla F. A biochemical analysis of human periodontal tissue proteoglycans. Biochem. J. 1992: 284: 267–274

30. Mongiat M, Otto J, Oldershaw R, Ferrer F, Sato J D, Iozzo RV. Fibroblast growth factor-binding protein is a novel partner for perlecan protein core. J. Biol. Chem. 2001: 30: 10263–10271

31. Mongiat M, Taylor K, Otto J, Aho S, Uitto J, Whitelock J M, Iozzo R V. The protein core of the proteoglycan perlecan binds specifically to fibroblast growth factor-7. J. Biol. Chem. 2000: 275: 7095–7100

32. Murdoch A D, Dodge G R, Cohen I, Tuan R S, Iozzo R V. Primary structure of the human heparan sulfate proteoglycan from basement membrane (HSPG2/perlecan)—a chimeric molecule with multiple domains homologous to the low density lipoprotein receptor, laminin, neural cell adhesion molecules, and epidermal growth factor. J. Biol. Chem. 1992: 267: 8544–8557

33. Murdoch A D, Liu B, Schwarting R, Tuan R S, Iozzo R V. Widespread expression of perlecan proteoglycan in basement membranes and extracellular matrices of human tissues as detected by a novel monoclonal antibody against domain III and by in situ hybridization. J. Histochem. Cytochem 1994: 42: 239–249

34. Myers R. Immunology: A Laboratory Manual. Ed. McGraw-Hill Science, 1994: 144.

35. Nissen N N, Shankar R, Gamelli R L, Singh A, DiPietro L A. Heparin and heparan sulphate protect basic fibroblast growth factor from non-enzymic glycosylation. Biochem. J. 1999: 338: 637–642

36. Noonan D M, Fulle A, Valente P, Cai S, Horigan E, Sasaki M, Yamada Y, Hassell J R. The complete sequence of perlecan, a basement membrane heparan sulfate proteoglycan, reveals extensive similarity with laminin A chain, low density lipoprotein-receptor, and the neural cell adhesion molecule. J. Biol. Chem. 1991: 266(34): 22939–22947

37. Nugent M A, Iozzo R V. Fibroblast growth factor-2. Int. J. Biochem. Cell Biol. 2000: 32: 115–120

38. Oksala O, Salo T, Tammi R, Hakkinen L, Jalkanen M, Inki P, Larajava H. Expression of proteoglycans and hyaluronan during wound healing. J. Histochem. Cytochem 1995: 43: 125–135

39. Saku T, Furthmayr H. Characterisation of the major heparan sulfate proteoglycan secreted by bovine aortic endothelial cells in culture. J. Biol. Chem. 1989: 264: 3514–3523

40. Sharma B, Handler M, Eichstetter I, Whitelock J M, Nugent M A, Iozzo R V. Antisense targeting of perlecan blocks tumor growth and angiogenesis in vivo. J. Clin. Invest. 1998: 102: 1599–1608

41. Shi Z, Zeng M, Yang G, Seigel F, Cain L J, van Kampen K R, Elmets C A, Tang D-CC. Protection against tetanus by needle-free inoculation of adenovirus-vectored nasal and epicutaneous vaccines. Journal of Virology 2001: 75: 11474–11482

42. Sundarraj N, Fite D, Belak R, Sudarraj S, Rada J, Okamoto S, Hassell J. Proteoglycan distribution during healing of corneal stromal wounds in chick. Exp. Eye Res. 1998: 67: 433–442

43. Sundarraj N, Fite D, Ledbetter S, Chakravarti S, Hassell J R. Perlecan is a component of cartilage matrix and promotes chondrocyte attachment. J. Cell Sci. 1995: 108: 2663–2672

44. Tolsma S S, Stack M S, Bouck N. Lumen formation and other angiogenic activities of cultured capillary endothelial cells are inhibited by thrombospondin-1. Microvasc. Res. 1997: 54: 13–26

45. Vischer P, Feitsma K, Schon P, Volker W. Perlecan is responsible for thrombospondin 1 binding on the cell surface of cultured porcine endothelial cells. Eur. J. Cell Biol. 1997: 73: 332–343

46. Whitelock J M, Graham L D, Melrose J, Iozzo R V, Underwood P A. Human perlecan immunopurified from different endothelial cell sources has different adhesive properties for vascular cells. Matrix Biol. 1999: 18: 163–178

47. Whitelock J M, Murdoch A D, Iozzo R V, Underwood P A. The degradation of human endothelial cell-derived perlecan and release of bound basic fibroblast growth factor by stromelysin, collagenase, plasmin, and heparanases. J. Biol. Chem. 1996: 271: 10079–10086

48. Yu W H, Woessner J F, Jr. Heparan sulfate proteoglycans as extracellular docking molecules for matrilysin (matrix metalloproteinase 7). J. Biol. Chem. 2000: 275: 183–191

What is claimed is:

1. A method for effective healing of a wound or a cutaneous injury in a subject in need of such healing via delivery of a heparan sulfate-decorated perlecan molecule, the method comprising administering to a site of the wound or cutaneous injury in the subject a composition comprising a viral vector or liposome comprising a nucleic acid coding for perlecan and a pharmaceutically acceptable carrier or diluent, whereby a heparan sulfate-decorated perlecan is generated at the site of the wound or the cutaneous injury by the subject, said nucleic acid being delivered in an amount sufficient to deliver an effective amount of heparan sulfate to the wound or the cutaneous injury resulting in an improvement in effective healing of the wounds or the cutaneous injury in the subject.

2. The method of claim 1 where the nucleic acid has the sequence of SEQ ID NO: 5.

3. The method of claim 1 where the viral vector is an adenoviral vector.

* * * * *